(12) United States Patent
Dahlgren et al.

(10) Patent No.: US 9,744,038 B2
(45) Date of Patent: Aug. 29, 2017

(54) MEDICAL DEVICE FOR CONSTRICTING TISSUE OR A BODILY ORIFICE, FOR EXAMPLE A MITRAL VALVE

(75) Inventors: Jon Dahlgren, Surrey (CA); Doug Goertzen, New Westminster (CA); Daniel Gelbart, Vancouver (CA)

(73) Assignee: KARDIUM INC., Burnaby (CA)

( * ) Notice: Subject to any disclaimer, the term of this patent is extended or adjusted under 35 U.S.C. 154(b) by 0 days.

(21) Appl. No.: 12/899,407

(22) Filed: Oct. 6, 2010

(65) Prior Publication Data

US 2011/0022166 A1 Jan. 27, 2011

Related U.S. Application Data

(62) Division of application No. 12/120,195, filed on May 13, 2008, now abandoned.

(51) Int. Cl.
*A61M 31/00* (2006.01)
*A61F 2/24* (2006.01)
(Continued)

(52) U.S. Cl.
CPC ........ *A61F 2/2445* (2013.01); *A61B 17/0401* (2013.01); *A61B 17/0469* (2013.01);
(Continued)

(58) Field of Classification Search
CPC ................................................ A61B 17/0401
(Continued)

(56) References Cited

U.S. PATENT DOCUMENTS

| 566,521 A | 8/1896 | Leger |
| 3,132,438 A | 5/1964 | Ward et al. ..................... 43/53.5 |

(Continued)

FOREIGN PATENT DOCUMENTS

| EP | 0723467 | 4/2002 |
| EP | 2082690 | 7/2009 |

(Continued)

OTHER PUBLICATIONS

Athanasuleas et al., "Surgical Anterior Ventricular Restoration for Ischemic Cardiomyopathy," *Operative Techniques in Thoracic and Cardiovascular Surgery* 7(2):66-75, May 2002.

(Continued)

*Primary Examiner* — Thomas J Sweet
*Assistant Examiner* — Wade P Schutte
(74) *Attorney, Agent, or Firm* — Rossi, Kimms & McDowell LLP

(57) ABSTRACT

A medical apparatus positionable in a cavity of a bodily organ (e.g., a heart) may constrict a bodily orifice (e.g., a mitral valve). The medical apparatus may include tissue anchors that are implanted in the annulus of the orifice. The tissue anchors may be guided into position by an intravascularly or percutaneously deployed anchor guiding frame. Constriction of the orifice may be accomplished by cinching a flexible cable attached to implanted tissue anchors. The medical device may be used to approximate the septal and lateral (clinically referred to as anterior and posterior) annulus of the mitral valve in order to move the posterior leaflet anteriorly and the anterior leaflet posteriorly and thereby improve leaflet coaptation and eliminate mitral regurgitation.

27 Claims, 18 Drawing Sheets

(51) Int. Cl.
*A61B 17/04* (2006.01)
*A61B 17/00* (2006.01)
*A61B 17/22* (2006.01)

(52) U.S. Cl.
CPC . *A61B 17/0485* (2013.01); *A61B 2017/00331* (2013.01); *A61B 2017/0409* (2013.01); *A61B 2017/0437* (2013.01); *A61B 2017/0441* (2013.01); *A61B 2017/0464* (2013.01); *A61B 2017/0496* (2013.01); *A61B 2017/22038* (2013.01); *A61F 2/2454* (2013.01)

(58) Field of Classification Search
USPC .................. 623/2.36, 2.37; 606/228
See application file for complete search history.

(56) References Cited

U.S. PATENT DOCUMENTS

| | | | |
|---|---|---|---|
| 4,041,955 A | 8/1977 | Kelly et al. | 128/419 P |
| 4,085,744 A | 4/1978 | Lewis et al. | 128/69 |
| 4,114,202 A | 9/1978 | Roy et al. | 3/1.5 |
| 4,164,046 A | 8/1979 | Cooley | 3/1.5 |
| 4,225,148 A | 9/1980 | Andersson | 280/95 R |
| 4,240,441 A | 12/1980 | Khalil | 128/692 |
| 4,261,342 A | 4/1981 | Aranguren Duo | 128/1 R |
| 4,263,680 A | 4/1981 | Reul et al. | 3/1.5 |
| 4,273,128 A | 6/1981 | Lary | 128/305 |
| 4,411,266 A | 10/1983 | Cosman | 128/303.18 |
| 4,490,859 A | 1/1985 | Black et al. | 3/1.5 |
| 4,527,554 A | 7/1985 | Klein | 128/92 B |
| 4,543,090 A | 9/1985 | McCoy | 604/95 |
| 4,699,147 A | 10/1987 | Chilson et al. | 128/642 |
| 4,770,187 A | 9/1988 | Lash et al. | 128/760 |
| 4,794,912 A | 1/1989 | Lia | 128/4 |
| 4,850,957 A | 7/1989 | Summers | 604/22 |
| 4,887,613 A | 12/1989 | Farr et al. | 606/159 |
| 4,890,602 A | 1/1990 | Hake | 128/4 |
| 4,890,612 A | 1/1990 | Kensey | 606/213 |
| 4,893,613 A | 1/1990 | Hake | 128/4 |
| 4,895,166 A | 1/1990 | Farr et al. | 128/751 |
| 4,921,499 A | 5/1990 | Hoffman et al. | 623/16 |
| 4,942,788 A | 7/1990 | Farr et al. | 76/115 |
| 4,979,514 A | 12/1990 | Sekii et al. | 128/713 |
| 4,994,698 A | 2/1991 | Kliman et al. | 310/81 |
| 4,998,933 A | 3/1991 | Eggers et al. | 606/41 |
| 5,021,059 A | 6/1991 | Kensey et al. | 606/213 |
| 5,026,384 A | 6/1991 | Farr et al. | 606/159 |
| 5,039,894 A | 8/1991 | Teter et al. | 310/26 |
| 5,047,047 A | 9/1991 | Yoon | 606/216 |
| 5,100,418 A | 3/1992 | Yoon et al. | 606/139 |
| 5,104,399 A | 4/1992 | Lazarus | 623/1 |
| 5,122,137 A | 6/1992 | Lennox | 606/40 |
| 5,127,902 A | 7/1992 | Fischell | 604/22 |
| 5,156,151 A | 10/1992 | Imran | 128/642 |
| 5,156,609 A | 10/1992 | Nakao et al. | 606/142 |
| 5,174,299 A | 12/1992 | Nelson | 128/642 |
| 5,176,693 A | 1/1993 | Pannek, Jr. | 606/159 |
| 5,178,620 A | 1/1993 | Eggers et al. | 606/41 |
| 5,192,291 A | 3/1993 | Pannek, Jr. | 606/159 |
| 5,192,314 A | 3/1993 | Daskalakis | 623/3 |
| 5,201,316 A | 4/1993 | Pomeranz et al. | 128/662.06 |
| 5,228,442 A | 7/1993 | Imran | 128/642 |
| 5,242,386 A | 9/1993 | Holzer | 604/22 |
| 5,242,456 A | 9/1993 | Nash et al. | |
| 5,245,987 A | 9/1993 | Redmond et al. | 128/20 |
| 5,258,000 A | 11/1993 | Gianturco | 606/151 |
| 5,279,299 A | 1/1994 | Imran | 128/642 |
| 5,293,869 A | 3/1994 | Edwards et al. | 128/642 |
| 5,312,435 A | 5/1994 | Nash et al. | 606/213 |
| 5,312,439 A | 5/1994 | Loeb | 607/2 |
| 5,317,952 A | 6/1994 | Immega | 91/418 |
| 5,320,632 A | 6/1994 | Heidmueller | 606/144 |
| 5,341,807 A | 8/1994 | Nardella | 128/642 |
| 5,364,408 A | 11/1994 | Gordon | 606/144 |
| 5,366,443 A | 11/1994 | Eggers et al. | 604/114 |
| 5,366,459 A | 11/1994 | Yoon | 606/151 |
| 5,368,601 A | 11/1994 | Sauer et al. | 606/144 |
| 5,374,275 A | 12/1994 | Bradley et al. | 606/144 |
| 5,375,612 A | 12/1994 | Cottenceau et al. | |
| 5,379,773 A | 1/1995 | Hornsby | 128/662.06 |
| 5,383,887 A | 1/1995 | Nadal | |
| RE34,866 E | 2/1995 | Kensey et al. | |
| 5,390,664 A | 2/1995 | Redmond et al. | 128/20 |
| 5,417,698 A | 5/1995 | Green et al. | 606/139 |
| 5,419,767 A | 5/1995 | Eggers et al. | 604/114 |
| 5,423,859 A * | 6/1995 | Koyfman et al. | 606/228 |
| 5,450,860 A | 9/1995 | O'Connor | 128/898 |
| 5,454,834 A * | 10/1995 | Boebel et al. | 606/228 |
| 5,462,561 A * | 10/1995 | Voda | A61B 17/0057 112/169 |
| 5,478,353 A | 12/1995 | Yoon | 606/213 |
| 5,496,267 A | 3/1996 | Drasler et al. | 604/22 |
| 5,507,811 A | 4/1996 | Koike et al. | |
| 5,531,760 A | 7/1996 | Alwafaie | 606/216 |
| 5,557,967 A | 9/1996 | Renger | 73/204.24 |
| 5,558,091 A | 9/1996 | Acker et al. | |
| 5,575,810 A | 11/1996 | Swanson et al. | |
| 5,593,424 A | 1/1997 | Northrup, III | 606/232 |
| 5,598,848 A | 2/1997 | Swanson et al. | 128/696 |
| 5,634,942 A | 6/1997 | Chevillon et al. | |
| 5,645,566 A | 7/1997 | Brenneman et al. | |
| 5,662,587 A | 9/1997 | Grundfest et al. | 600/114 |
| 5,681,308 A | 10/1997 | Edwards et al. | 606/41 |
| 5,681,336 A | 10/1997 | Clement et al. | 606/159 |
| 5,687,723 A | 11/1997 | Avitall | 128/642 |
| 5,690,649 A | 11/1997 | Li | 606/139 |
| 5,697,285 A | 12/1997 | Nappi et al. | 91/519 |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,730,127 A | 3/1998 | Avitall | 128/642 |
| 5,752,965 A | 5/1998 | Francis et al. | |
| 5,762,066 A | 6/1998 | Law et al. | 128/660.03 |
| 5,769,846 A | 6/1998 | Edwards et al. | 606/41 |
| 5,782,239 A | 7/1998 | Webster, Jr. | 128/642 |
| 5,782,861 A | 7/1998 | Cragg et al. | 606/216 |
| 5,782,879 A | 7/1998 | Rosborough et al. | 607/6 |
| 5,800,495 A | 9/1998 | Machek et al. | 607/116 |
| 5,824,066 A | 10/1998 | Gross | 623/2 |
| 5,830,222 A | 11/1998 | Makower | |
| 5,836,990 A | 11/1998 | Li | 607/28 |
| 5,865,791 A | 2/1999 | Whayne et al. | 604/49 |
| 5,871,505 A | 2/1999 | Adams et al. | 607/5 |
| 5,876,343 A | 3/1999 | Teo | 600/443 |
| 5,881,727 A | 3/1999 | Edwards | 128/642 |
| 5,891,136 A | 4/1999 | McGee et al. | 606/41 |
| 5,904,711 A | 5/1999 | Flom et al. | 607/129 |
| 5,919,207 A | 7/1999 | Taheri | 606/219 |
| 5,921,924 A | 7/1999 | Avitall | 600/374 |
| 5,935,075 A | 8/1999 | Casscells et al. | 600/474 |
| 5,935,079 A | 8/1999 | Swanson et al. | 600/509 |
| 5,941,251 A | 8/1999 | Panescu et al. | 128/899 |
| 5,961,440 A | 10/1999 | Schweich, Jr. et al. | 600/16 |
| 5,964,782 A | 10/1999 | Lafontaine et al. | 606/213 |
| 5,971,994 A | 10/1999 | Fritzsch | |
| 5,976,174 A | 11/1999 | Ruiz | |
| 5,980,473 A | 11/1999 | Korakianitis et al. | 600/587 |
| 5,984,950 A | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,063,082 A | 5/2000 | DeVore et al. | 606/45 |
| 6,074,417 A | 6/2000 | Peredo | 623/2 |
| 6,074,418 A | 6/2000 | Buchanan et al. | |
| 6,104,944 A | 8/2000 | Martinelli | 600/424 |
| 6,113,610 A | 9/2000 | Poncet | 606/139 |
| 6,123,702 A | 9/2000 | Swanson et al. | |
| 6,132,438 A | 10/2000 | Fleischman et al. | |
| 6,138,043 A | 10/2000 | Avitall | 600/377 |
| 6,142,993 A | 11/2000 | Whayne et al. | 606/41 |
| 6,156,046 A | 12/2000 | Passafaro et al. | 606/159 |
| 6,183,496 B1 | 2/2001 | Urbanski | |
| 6,203,554 B1 | 3/2001 | Roberts | 606/144 |
| 6,210,432 B1 | 4/2001 | Solem et al. | 623/1.15 |

(56) References Cited

U.S. PATENT DOCUMENTS

| | | | |
|---|---|---|---|
| 6,214,032 B1 | 4/2001 | Loeb et al. | 607/1 |
| 6,217,573 B1 | 4/2001 | Webster | 606/41 |
| 6,221,103 B1 | 4/2001 | Melvin | 623/3.1 |
| 6,221,104 B1 | 4/2001 | Buckberg et al. | 623/3.1 |
| 6,231,561 B1 * | 5/2001 | Frazier | A61B 17/00234 |
| | | | 604/500 |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |
| 6,261,309 B1 | 7/2001 | Urbanski | |
| 6,266,550 B1 | 7/2001 | Selmon et al. | 600/407 |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,308,091 B1 | 10/2001 | Avitall | 600/374 |
| 6,332,864 B1 | 12/2001 | Schweich, Jr. et al. | 600/16 |
| 6,346,105 B1 | 2/2002 | Tu et al. | 606/41 |
| 6,358,258 B1 | 3/2002 | Arcia et al. | 606/139 |
| 6,358,277 B1 | 3/2002 | Duran | 623/2.12 |
| 6,360,749 B1 | 3/2002 | Jayaraman | 128/898 |
| 6,379,366 B1 | 4/2002 | Fleischman et al. | 606/139 |
| 6,383,151 B1 | 5/2002 | Diederich et al. | 601/2 |
| 6,389,311 B1 | 5/2002 | Whayne et al. | 600/523 |
| 6,391,048 B1 | 5/2002 | Ginn et al. | 606/213 |
| 6,391,054 B2 | 5/2002 | Carpentier et al. | 623/2.37 |
| 6,402,680 B2 | 6/2002 | Mortier et al. | 600/16 |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |
| 6,416,459 B1 | 7/2002 | Haindl | 600/37 |
| 6,432,115 B1 | 8/2002 | Mollenauer et al. | 606/148 |
| 6,436,052 B1 | 8/2002 | Nikolic et al. | 600/529 |
| 6,450,171 B1 | 9/2002 | Buckberg et al. | 128/898 |
| 6,475,223 B1 | 11/2002 | Werp et al. | 606/108 |
| 6,485,409 B1 | 11/2002 | Voloshin et al. | 600/115 |
| 6,485,489 B2 | 11/2002 | Teirstein et al. | 606/41 |
| 6,506,210 B1 | 1/2003 | Kanner | 606/213 |
| 6,514,249 B1 | 2/2003 | Maguire et al. | 606/41 |
| 6,529,756 B1 | 3/2003 | Phan et al. | 600/374 |
| 6,537,198 B1 | 3/2003 | Vidlund et al. | 600/16 |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,582,447 B1 | 6/2003 | Patel et al. | |
| 6,589,208 B2 | 7/2003 | Ewers et al. | 604/104 |
| 6,626,930 B1 | 9/2003 | Allen et al. | 606/213 |
| 6,632,238 B2 | 10/2003 | Ginn et al. | 606/213 |
| 6,662,034 B2 | 12/2003 | Segner et al. | 600/373 |
| 6,676,685 B2 | 1/2004 | Pedros et al. | 606/213 |
| 6,681,773 B2 | 1/2004 | Murphy et al. | 128/898 |
| 6,704,590 B2 | 3/2004 | Haldeman | 600/407 |
| 6,723,038 B1 | 4/2004 | Schroeder et al. | 600/16 |
| 6,726,704 B1 | 4/2004 | Loshakove et al. | 606/213 |
| 6,726,716 B2 | 4/2004 | Marquez | 623/2.36 |
| 6,743,241 B2 | 6/2004 | Kerr | 606/144 |
| 6,749,622 B2 | 6/2004 | McGuckin, Jr. et al. | 606/213 |
| 6,752,810 B1 | 6/2004 | Gao et al. | 606/103 |
| 6,760,616 B2 | 7/2004 | Hoey et al. | 600/547 |
| 6,780,197 B2 | 8/2004 | Roe et al. | 606/213 |
| 6,797,001 B2 | 9/2004 | Mathis et al. | 623/2.37 |
| 6,800,090 B2 | 10/2004 | Alferness et al. | 623/2.36 |
| 6,824,562 B2 | 11/2004 | Mathis et al. | |
| 6,837,886 B2 | 1/2005 | Collins et al. | 606/41 |
| 6,840,957 B2 | 1/2005 | DiMatteo et al. | |
| 6,852,076 B2 | 2/2005 | Nikolic et al. | 600/37 |
| 6,855,143 B2 | 2/2005 | Davison et al. | 606/41 |
| 6,881,218 B2 | 4/2005 | Beyer et al. | |
| 6,890,353 B2 | 5/2005 | Cohn et al. | 623/2.37 |
| 6,892,091 B1 | 5/2005 | Ben-Haim et al. | 600/509 |
| 6,899,674 B2 | 5/2005 | Viebach et al. | 600/152 |
| 6,907,297 B2 | 6/2005 | Wellman et al. | 607/122 |
| 6,908,478 B2 | 6/2005 | Alferness et al. | 623/1.11 |
| 6,913,576 B2 | 7/2005 | Bowman | 606/505 |
| 6,918,903 B2 | 7/2005 | Bass | 604/511 |
| 6,926,669 B1 | 8/2005 | Stewart et al. | 600/439 |
| 6,941,171 B2 | 9/2005 | Mann et al. | 607/39 |
| 6,942,657 B2 | 9/2005 | Sinofsky et al. | 606/15 |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,010 B2 | 1/2006 | Francischelli et al. | 606/42 |
| 6,989,028 B2 | 1/2006 | Lashinski et al. | 623/2.37 |
| 6,991,649 B2 | 1/2006 | Sievers | 623/2.23 |
| 6,994,093 B2 | 2/2006 | Murphy et al. | 128/898 |
| 6,997,951 B2 | 2/2006 | Solem et al. | 623/2.37 |
| 7,001,383 B2 | 2/2006 | Keidar | 606/41 |
| 7,025,776 B1 | 4/2006 | Houser et al. | 606/213 |
| 7,050,848 B2 | 5/2006 | Hoey et al. | 600/547 |
| 7,052,487 B2 | 5/2006 | Cohn et al. | 604/509 |
| 7,068,867 B2 | 6/2006 | Adoram et al. | 385/12 |
| 7,101,395 B2 | 9/2006 | Tremulis et al. | 623/2.11 |
| 7,141,019 B2 | 11/2006 | Pearlman | 600/437 |
| 7,144,363 B2 | 12/2006 | Pai et al. | 600/16 |
| 7,160,322 B2 | 1/2007 | Gabbay | 623/2.36 |
| 7,166,127 B2 | 1/2007 | Spence et al. | 623/2.37 |
| 7,177,677 B2 | 2/2007 | Kaula et al. | 600/546 |
| 7,186,210 B2 | 3/2007 | Feld et al. | 600/16 |
| 7,187,964 B2 | 3/2007 | Khoury | 600/509 |
| 7,189,202 B2 | 3/2007 | Lau et al. | 600/37 |
| 7,276,044 B2 | 10/2007 | Ferry et al. | 604/95.01 |
| 7,279,007 B2 | 10/2007 | Nikolic et al. | 623/11.11 |
| 7,280,863 B2 | 10/2007 | Shachar | |
| 7,300,435 B2 | 11/2007 | Wham et al. | 606/34 |
| 7,303,526 B2 | 12/2007 | Sharkey et al. | 600/37 |
| 7,320,665 B2 | 1/2008 | Vijay | 600/17 |
| 7,335,196 B2 | 2/2008 | Swanson et al. | 606/41 |
| 7,374,530 B2 | 5/2008 | Schaller | 600/16 |
| 7,399,271 B2 | 7/2008 | Khairkhahan et al. | 600/16 |
| 7,413,568 B2 | 8/2008 | Swanson et al. | |
| 7,431,726 B2 * | 10/2008 | Spence | A61B 17/0401 |
| | | | 606/151 |
| 7,452,325 B2 | 11/2008 | Schaller | 600/37 |
| 7,452,375 B2 | 11/2008 | Mathis et al. | 623/2.36 |
| 7,507,252 B2 | 3/2009 | Lashinski et al. | 623/2.37 |
| 7,513,867 B2 | 4/2009 | Lichtenstein | 600/37 |
| 7,582,051 B2 | 9/2009 | Khairkhahan et al. | 600/16 |
| 7,611,534 B2 | 11/2009 | Kapadia et al. | |
| 7,674,276 B2 | 3/2010 | Stone et al. | 606/232 |
| 7,704,277 B2 | 4/2010 | Zakay et al. | |
| 7,736,388 B2 | 6/2010 | Goldfarb et al. | |
| 7,738,967 B2 | 6/2010 | Salo | 607/116 |
| 7,749,249 B2 | 7/2010 | Gelbart et al. | |
| 7,837,610 B2 | 11/2010 | Lichtenstein et al. | 600/16 |
| 7,869,854 B2 | 1/2011 | Shachar et al. | |
| 7,873,402 B2 | 1/2011 | Shachar | |
| 7,887,482 B2 | 2/2011 | Hamada | 600/233 |
| 8,027,714 B2 | 9/2011 | Shachar | |
| 8,128,644 B2 | 3/2012 | Carley et al. | |
| 8,150,499 B2 | 4/2012 | Gelbart et al. | |
| 8,337,524 B2 | 12/2012 | Gelbart et al. | |
| 8,449,605 B2 | 5/2013 | Lichtenstein et al. | |
| 8,532,746 B2 | 9/2013 | Gelbart et al. | |
| 8,672,998 B2 | 3/2014 | Lichtenstein et al. | |
| 2001/0003158 A1 | 6/2001 | Kensey et al. | 606/213 |
| 2001/0005787 A1 | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2001/0041915 A1 | 11/2001 | Roue et al. | |
| 2001/0044568 A1 | 11/2001 | Langberg et al. | 600/37 |
| 2002/0002329 A1 | 1/2002 | Avitall | 600/377 |
| 2002/0013621 A1 | 1/2002 | Stobie et al. | |
| 2002/0016628 A1 | 2/2002 | Langberg et al. | 623/2.36 |
| 2002/0026092 A1 | 2/2002 | Buckberg et al. | 600/37 |
| 2002/0055775 A1 | 5/2002 | Carpentier et al. | 623/2.17 |
| 2002/0082621 A1 | 6/2002 | Schurr et al. | 606/151 |
| 2002/0087156 A1 | 7/2002 | Maguire et al. | 606/41 |
| 2002/0087173 A1 | 7/2002 | Alferness et al. | 606/151 |
| 2002/0107478 A1 | 8/2002 | Wendlandt | 604/95.01 |
| 2002/0107511 A1 | 8/2002 | Collins et al. | 606/41 |
| 2002/0107530 A1 | 8/2002 | Sauer et al. | 606/139 |
| 2002/0111647 A1 | 8/2002 | Khairkhahan et al. | |

(56) References Cited

U.S. PATENT DOCUMENTS

| | | | |
|---|---|---|---|
| 2002/0115944 A1 | 8/2002 | Mendes et al. | 600/594 |
| 2002/0133143 A1 | 9/2002 | Murphy et al. | |
| 2002/0161394 A1 | 10/2002 | Macoviak et al. | 606/200 |
| 2002/0161406 A1 | 10/2002 | Silvian | 607/5 |
| 2002/0169359 A1 | 11/2002 | McCarthy et al. | 600/16 |
| 2002/0169360 A1 | 11/2002 | Taylor et al. | 600/37 |
| 2002/0169504 A1 | 11/2002 | Alferness et al. | 623/2.36 |
| 2002/0177782 A1 | 11/2002 | Penner | 600/485 |
| 2002/0183836 A1 | 12/2002 | Liddicoat et al. | 623/2.11 |
| 2002/0183841 A1 | 12/2002 | Cohn et al. | 623/2.36 |
| 2002/0188170 A1 | 12/2002 | Santamore et al. | 600/37 |
| 2002/0198603 A1 | 12/2002 | Buckberg et al. | 623/23.71 |
| 2003/0018358 A1 | 1/2003 | Saadat | |
| 2003/0023241 A1 | 1/2003 | Drewry et al. | 606/74 |
| 2003/0028202 A1 | 2/2003 | Sancoff et al. | 606/144 |
| 2003/0036755 A1 | 2/2003 | Ginn | |
| 2003/0045896 A1 | 3/2003 | Murphy et al. | 606/191 |
| 2003/0050682 A1 | 3/2003 | Sharkey et al. | 607/126 |
| 2003/0050685 A1 | 3/2003 | Nikolic et al. | 623/1.11 |
| 2003/0050693 A1 | 3/2003 | Quijano et al. | |
| 2003/0069570 A1 | 4/2003 | Witzel et al. | 606/28 |
| 2003/0069593 A1 | 4/2003 | Tremulis et al. | |
| 2003/0069636 A1 | 4/2003 | Solem et al. | 623/2.37 |
| 2003/0078465 A1 | 4/2003 | Pai et al. | 600/16 |
| 2003/0078652 A1 | 4/2003 | Sutherland | 623/2.12 |
| 2003/0078671 A1 | 4/2003 | Lesniak et al. | 623/23.64 |
| 2003/0083742 A1 | 5/2003 | Spence et al. | |
| 2003/0105384 A1 | 6/2003 | Sharkey et al. | 600/16 |
| 2003/0105520 A1 | 6/2003 | Alferness et al. | 623/2.36 |
| 2003/0109770 A1 | 6/2003 | Sharkey et al. | 600/16 |
| 2003/0124480 A1 | 7/2003 | Peacock | 433/23 |
| 2003/0149333 A1 | 8/2003 | Alferness | 600/16 |
| 2003/0158570 A1 | 8/2003 | Ferrazzi | 606/191 |
| 2003/0163191 A1 | 8/2003 | Nikolic et al. | 623/1.11 |
| 2003/0167055 A1 | 9/2003 | Kolata et al. | |
| 2003/0181819 A1 | 9/2003 | Desai | 600/510 |
| 2003/0208210 A1 | 11/2003 | Dreyfuss et al. | 606/144 |
| 2003/0212453 A1 | 11/2003 | Mathis et al. | 632/2.11 |
| 2003/0220667 A1 | 11/2003 | van der Burg et al. | 606/200 |
| 2003/0229395 A1 | 12/2003 | Cox | 623/2.36 |
| 2004/0002626 A1 | 1/2004 | Feld et al. | 600/37 |
| 2004/0054279 A1 | 3/2004 | Hanley | 600/424 |
| 2004/0122516 A1 | 6/2004 | Fogarty et al. | |
| 2004/0127916 A1 | 7/2004 | Bolduc et al. | |
| 2004/0133220 A1 | 7/2004 | Lashinski et al. | |
| 2004/0133273 A1 | 7/2004 | Cox | 623/2.11 |
| 2004/0138529 A1 | 7/2004 | Wiltshire et al. | 600/144 |
| 2004/0138744 A1 | 7/2004 | Lashinski et al. | 623/2.36 |
| 2004/0138745 A1 | 7/2004 | Macoviak et al. | |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0176797 A1 | 9/2004 | Opolski | 606/213 |
| 2004/0176800 A1 | 9/2004 | Paraschac et al. | |
| 2004/0186566 A1 | 9/2004 | Hindrichs et al. | 623/2.37 |
| 2004/0193187 A1 | 9/2004 | Boehringer et al. | 606/144 |
| 2004/0215232 A1 | 10/2004 | Belhe et al. | 606/213 |
| 2004/0220593 A1 | 11/2004 | Greenhalgh | |
| 2004/0236419 A1 | 11/2004 | Milo | |
| 2004/0243170 A1 | 12/2004 | Suresh et al. | 606/198 |
| 2004/0249408 A1 | 12/2004 | Murphy et al. | 606/198 |
| 2004/0249453 A1 | 12/2004 | Cartledge et al. | 623/2.37 |
| 2004/0260390 A1 | 12/2004 | Sarac et al. | 623/1.24 |
| 2004/0260393 A1 | 12/2004 | Rahdert et al. | |
| 2004/0267191 A1 | 12/2004 | Gifford, III et al. | |
| 2004/0267358 A1 | 12/2004 | Reitan | 623/2.37 |
| 2005/0004668 A1 | 1/2005 | Aklog et al. | 623/2.36 |
| 2005/0015109 A1 | 1/2005 | Lichtenstein | 606/200 |
| 2005/0038509 A1 | 2/2005 | Ashe | 623/2.36 |
| 2005/0054938 A1 | 3/2005 | Wehman et al. | 600/483 |
| 2005/0055089 A1 | 3/2005 | Macoviak et al. | 623/2.37 |
| 2005/0060030 A1 | 3/2005 | Lashinski et al. | 623/2.37 |
| 2005/0064665 A1 | 3/2005 | Han | 438/286 |
| 2005/0065420 A1 | 3/2005 | Collins et al. | 600/374 |
| 2005/0065504 A1 | 3/2005 | Melsky et al. | 606/16 |
| 2005/0075727 A1 | 4/2005 | Wheatley | 623/2.17 |
| 2005/0080402 A1 | 4/2005 | Santamore et al. | 606/1 |
| 2005/0090840 A1 | 4/2005 | Gerbino et al. | 606/148 |
| 2005/0096047 A1 | 5/2005 | Haberman et al. | 455/432.3 |
| 2005/0096498 A1 | 5/2005 | Hauser et al. | |
| 2005/0096589 A1 | 5/2005 | Shachar | |
| 2005/0096647 A1 | 5/2005 | Steinke et al. | |
| 2005/0107723 A1 | 5/2005 | Wehman et al. | 600/595 |
| 2005/0107871 A1 | 5/2005 | Realyvasquez et al. | 623/2.11 |
| 2005/0125030 A1 | 6/2005 | Forsberg et al. | 606/213 |
| 2005/0131441 A1 | 6/2005 | Iio et al. | |
| 2005/0137659 A1 | 6/2005 | Garabedian et al. | |
| 2005/0137689 A1 | 6/2005 | Salahieh et al. | |
| 2005/0137695 A1 | 6/2005 | Salahieh et al. | |
| 2005/0137700 A1 | 6/2005 | Spence et al. | 623/2.36 |
| 2005/0143809 A1 | 6/2005 | Salahieh et al. | |
| 2005/0148892 A1 | 7/2005 | Desai | 600/510 |
| 2005/0149014 A1 | 7/2005 | Hauck et al. | 606/41 |
| 2005/0149114 A1 | 7/2005 | Cartledge et al. | 606/213 |
| 2005/0154252 A1 | 7/2005 | Sharkey et al. | 600/37 |
| 2005/0177180 A1 | 8/2005 | Kaganov et al. | 606/151 |
| 2005/0177227 A1 | 8/2005 | Heim et al. | 623/2.12 |
| 2005/0182365 A1 | 8/2005 | Hennemann et al. | 604/113 |
| 2005/0187620 A1 | 8/2005 | Pai et al. | 623/2.37 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0197716 A1 | 9/2005 | Sharkey et al. | 623/23.67 |
| 2005/0203558 A1 | 9/2005 | Maschke | 606/180 |
| 2005/0209636 A1 | 9/2005 | Widomski et al. | 606/213 |
| 2005/0216052 A1 | 9/2005 | Mazzocchi et al. | 606/200 |
| 2005/0216054 A1 | 9/2005 | Widomski et al. | 606/213 |
| 2005/0240249 A1 | 10/2005 | Tu et al. | 607/96 |
| 2005/0251116 A1 | 11/2005 | Steinke et al. | 606/8 |
| 2005/0251132 A1 | 11/2005 | Oral et al. | 606/41 |
| 2005/0256521 A1 | 11/2005 | Kozel | 606/41 |
| 2005/0267573 A9 | 12/2005 | Macoviak et al. | |
| 2005/0267574 A1 | 12/2005 | Cohn et al. | 623/2.36 |
| 2005/0273138 A1 | 12/2005 | To et al. | |
| 2006/0004424 A1 | 1/2006 | Loeb et al. | 607/63 |
| 2006/0009755 A1 | 1/2006 | Sra | 606/32 |
| 2006/0009756 A1 | 1/2006 | Francischelli et al. | 606/32 |
| 2006/0014998 A1 | 1/2006 | Sharkey et al. | 600/16 |
| 2006/0015002 A1 | 1/2006 | Moaddeb et al. | 600/37 |
| 2006/0015003 A1 | 1/2006 | Moaddes et al. | 600/37 |
| 2006/0015038 A1 | 1/2006 | Weymarn-Scharli | 600/585 |
| 2006/0015096 A1 | 1/2006 | Hauck et al. | 606/41 |
| 2006/0025784 A1* | 2/2006 | Starksen et al. | 606/151 |
| 2006/0025800 A1 | 2/2006 | Suresh | 606/198 |
| 2006/0030881 A1 | 2/2006 | Sharkey et al. | 606/213 |
| 2006/0052867 A1 | 3/2006 | Revuelta et al. | |
| 2006/0058871 A1 | 3/2006 | Zakay et al. | 623/2.18 |
| 2006/0085049 A1 | 4/2006 | Cory et al. | 607/48 |
| 2006/0135968 A1 | 6/2006 | Schaller | 606/144 |
| 2006/0135970 A1 | 6/2006 | Schaller | 606/152 |
| 2006/0173536 A1 | 8/2006 | Mathis et al. | 623/2.11 |
| 2006/0184242 A1 | 8/2006 | Lichtenstein | 623/2.37 |
| 2006/0199995 A1 | 9/2006 | Vijay | 600/37 |
| 2006/0229491 A1 | 10/2006 | Sharkey et al. | 600/37 |
| 2006/0235286 A1 | 10/2006 | Stone et al. | 600/381 |
| 2006/0235314 A1 | 10/2006 | Migliuolo et al. | 600/505 |
| 2006/0241334 A1 | 10/2006 | Dubi et al. | 600/16 |
| 2006/0241745 A1 | 10/2006 | Solem | |
| 2006/0264980 A1 | 11/2006 | Khairkhahan et al. | 606/153 |
| 2006/0276683 A1 | 12/2006 | Feld et al. | 600/16 |
| 2006/0281965 A1 | 12/2006 | Khairkhahan et al. | 600/37 |
| 2006/0293698 A1 | 12/2006 | Douk | 606/142 |
| 2006/0293725 A1 | 12/2006 | Rubinsky et al. | 607/72 |
| 2007/0010817 A1 | 1/2007 | de Coninck | |
| 2007/0016006 A1 | 1/2007 | Shachar | |
| 2007/0016068 A1 | 1/2007 | Grunwald et al. | 600/468 |
| 2007/0016288 A1 | 1/2007 | Gurskis et al. | 623/2.11 |
| 2007/0027533 A1 | 2/2007 | Douk | |
| 2007/0038208 A1 | 2/2007 | Kefer | 606/34 |
| 2007/0050019 A1* | 3/2007 | Hyde | 623/2.36 |
| 2007/0060895 A1 | 3/2007 | Sibbitt et al. | |
| 2007/0083076 A1 | 4/2007 | Lichtenstein | 600/16 |
| 2007/0088362 A1 | 4/2007 | Bonutti et al. | 606/99 |
| 2007/0115390 A1 | 5/2007 | Makara et al. | 348/552 |

(56) References Cited

U.S. PATENT DOCUMENTS

| | | | |
|---|---|---|---|
| 2007/0118151 A1* | 5/2007 | Davidson | A61B 17/00234 606/144 |
| 2007/0118215 A1 | 5/2007 | Moaddeb | 623/2.37 |
| 2007/0129717 A1 | 6/2007 | Brown, III et al. | 606/41 |
| 2007/0135826 A1 | 6/2007 | Zaver et al. | |
| 2007/0135913 A1 | 6/2007 | Moaddeb et al. | 623/2.37 |
| 2007/0156233 A1 | 7/2007 | Kapadia et al. | |
| 2007/0161846 A1 | 7/2007 | Nikolic et al. | 600/16 |
| 2007/0185571 A1 | 8/2007 | Kapadia et al. | |
| 2007/0198057 A1 | 8/2007 | Gelbart et al. | |
| 2007/0198058 A1 | 8/2007 | Gelbart et al. | 606/213 |
| 2007/0213578 A1 | 9/2007 | Khairkhahan et al. | 600/16 |
| 2007/0213815 A1 | 9/2007 | Khairkhahan et al. | 623/3.1 |
| 2007/0219460 A1 | 9/2007 | Goldenberg | 600/566 |
| 2007/0225736 A1 | 9/2007 | Zeiner et al. | 606/148 |
| 2007/0249999 A1 | 10/2007 | Sklar et al. | 604/101.05 |
| 2007/0250160 A1 | 10/2007 | Rafiee | 623/2.11 |
| 2007/0270681 A1 | 11/2007 | Phillips et al. | |
| 2007/0270688 A1 | 11/2007 | Gelbart et al. | 600/427 |
| 2007/0270943 A1 | 11/2007 | Solem et al. | |
| 2007/0299343 A1 | 12/2007 | Waters | 600/43 |
| 2008/0004534 A1 | 1/2008 | Gelbart et al. | 600/508 |
| 2008/0004643 A1 | 1/2008 | To et al. | 606/159 |
| 2008/0004697 A1 | 1/2008 | Lichtenstein et al. | 623/2.11 |
| 2008/0033541 A1 | 2/2008 | Gelbart et al. | 623/2.11 |
| 2008/0045778 A1 | 2/2008 | Lichtenstein et al. | 600/16 |
| 2008/0051802 A1* | 2/2008 | Schostek et al. | 606/108 |
| 2008/0071298 A1 | 3/2008 | Khairkhahan et al. | 606/151 |
| 2008/0086164 A1 | 4/2008 | Rowe | 606/191 |
| 2008/0132915 A1 | 6/2008 | Buckman et al. | |
| 2008/0133002 A1 | 6/2008 | Gelbart et al. | |
| 2008/0140188 A1 | 6/2008 | Rahdert et al. | |
| 2008/0177300 A1 | 7/2008 | Mas et al. | |
| 2008/0228266 A1* | 9/2008 | McNamara | A61B 17/00234 623/2.36 |
| 2008/0262609 A1 | 10/2008 | Gross et al. | |
| 2008/0269785 A1 | 10/2008 | Lampropoulos et al. | 606/144 |
| 2008/0275477 A1 | 11/2008 | Sterrett et al. | 606/148 |
| 2008/0288060 A1 | 11/2008 | Kaye et al. | |
| 2008/0312713 A1 | 12/2008 | Wilfley et al. | 607/41 |
| 2009/0076597 A1 | 3/2009 | Dahlgren et al. | 623/2.1 |
| 2009/0131930 A1 | 5/2009 | Gelbart et al. | 606/41 |
| 2009/0157058 A1 | 6/2009 | Ferren et al. | 604/891.1 |
| 2009/0192441 A1 | 7/2009 | Gelbart et al. | 604/22 |
| 2009/0192527 A1 | 7/2009 | Messas | |
| 2009/0192539 A1 | 7/2009 | Lichtenstein | 606/191 |
| 2009/0204180 A1 | 8/2009 | Gelbart | 607/61 |
| 2009/0287304 A1 | 11/2009 | Dahlgren et al. | 623/2.37 |
| 2010/0087836 A1 | 4/2010 | Jaramillo et al. | 606/144 |
| 2010/0087837 A1 | 4/2010 | Jaramillo et al. | 606/144 |
| 2010/0161047 A1 | 6/2010 | Cabiri | |
| 2010/0179648 A1 | 7/2010 | Richter et al. | |
| 2010/0222789 A1 | 9/2010 | Gelbart et al. | 606/142 |
| 2011/0022166 A1 | 1/2011 | Dahlgren et al. | |
| 2011/0082538 A1 | 4/2011 | Dahlgren et al. | |
| 2011/0087203 A1 | 4/2011 | Lichtenstein et al. | 606/16 |
| 2011/0087227 A1 | 4/2011 | Mazur et al. | |
| 2011/0125172 A1 | 5/2011 | Gelbart et al. | 606/159 |
| 2011/0172658 A1 | 7/2011 | Gelbart et al. | 606/41 |
| 2011/0301618 A1 | 12/2011 | Lichtenstein | |
| 2012/0083806 A1 | 4/2012 | Goertzen | |
| 2012/0158016 A1 | 6/2012 | Gelbart et al. | 606/130 |
| 2012/0245604 A1 | 9/2012 | Tegzes | |
| 2013/0041405 A1 | 2/2013 | Gelbart et al. | |
| 2013/0238089 A1 | 9/2013 | Lichtenstein et al. | |
| 2013/0345797 A1 | 12/2013 | Dahlgren et al. | |
| 2014/0135913 A1 | 5/2014 | Lichtenstein et al. | |
| 2015/0223802 A1 | 8/2015 | Tegzes | |

FOREIGN PATENT DOCUMENTS

| | | |
|---|---|---|
| WO | 90/15582 | 12/1990 |
| WO | 95/10320 | 4/1995 |
| WO | 01/78625 | 10/2001 |
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/007031 A2 | 1/2005 |
| WO | 2005/046520 | 5/2005 |
| WO | 2005/070330 | 8/2005 |
| WO | 2005/102181 | 11/2005 |
| WO | 2006/017809 | 2/2006 |
| WO | 2006/105121 | 10/2006 |
| WO | 2006/135747 | 12/2006 |
| WO | 2006/135749 | 12/2006 |
| WO | 2007/021647 | 2/2007 |
| WO | 2007/115390 | 10/2007 |
| WO | 2008/002606 | 1/2008 |
| WO | 2009/065042 | 5/2009 |

OTHER PUBLICATIONS

Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.

Cardiac Implants, URL=http://nmtmedical.com/products/ci/index.htm, download date May 13, 2006, 1 page.

Cooley, "Ventricular Aneurysms and Akinesis," *Cleveland Clinic Quarterly* 45(1):130-132, 1978.

Dahlgren et al., "Medical Device, Kit and Method for Constricting Tissue or a Bodily Orifice, For Example a Mitral Valve," U.S. Appl. No. 61/278,232, filed Oct. 1, 2009, 215 pages.

Dahlgren et al., "Medical Device for Constricting Tissue or a Bodily Orifice, For Example a Mitral Valve," Office Action mailed Dec. 18, 2009, for U.S. Appl. No. 12/120,195, 9 pages.

Dahlgren et al., "Medical Device for Constricting Tissue or a Bodily Orifice, For Example a Mitral Valve," Amendment filed Apr. 13, 2010, for U.S. Appl. No. 12/120,195, 22 pages.

Dahlgren et al., "Medical Device for Constricting Tissue or a Bodily Orifice, For Example a Mitral Valve," Office Action mailed Jul. 7, 2010, for U.S. Appl. No. 12/120,195, 14 pages.

Dahlgren et al., "Medical Device, Kit and Method for Constricting Tissue or a Bodily Orifice, For Example a Mitral Valve," U.S. Appl. No. 12/894,912, filed Sep. 30, 2010, 135 pages.

David et al., "Postinfarction Ventricular Septal Rupture: Repair by Endocardial Patch with Infarct Exclusion," *Journal of Thoracic and Card Surgery* 110(5):1315-1322, 1995.

Dor et al., "Left Ventricular Aneurysm: A New Surgical Approach," *Thoracic Cardiovascular Surgery* 37:11-19, 1989.

Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.

Dor, "Left Ventricular Aneurysms: The Endoventricular Circular Patch Plasty," *Seminars in Thoracic and Cardiovascular Surgery* 9(2):123-130, Apr. 1997.

Gelbart et al., "Automatic Atherectomy System," U.S. Appl. No. 11/436,584, filed May 19, 2006, 16 pages.

Gelbart et al., "Method and Device for Closing Holes in Tissue," U.S. Appl. No. 11/436,585, filed May 19, 2006, 12 pages.

Gelbart et al., "Method and Device for Closing Holes in Tissue," Office Action mailed Sep. 4, 2008, for U.S. Appl. No. 11/436,585, 8 pages.

Gelbart et al., "Method and Device for Closing Holes in Tissue," Amendment filed Sep. 22, 2008, for U.S. Appl. No. 11/436,585, 3 pages.

Gelbart et al., "Method and Device for Closing Holes in Tissue," Office Action mailed Jan. 2, 2009, for U.S. Appl. No. 11/436,585, 11 pages.

Gelbart et al., "Method and Device for Closing Holes in Tissue," Amendment filed Jan. 30, 2009, for U.S. Appl. No. 11/436,585, 5 pages.

(56) References Cited

OTHER PUBLICATIONS

Gelbart et al., "Method and Device for Closing Holes in Tissue," Amendment filed Jun. 2, 2009, for U.S. Appl. No. 11/436,585, 7 pages.
Gelbart et al., "Method and Device for Closing Holes in Tissue," Office Action mailed Jul. 7, 2009, for U.S. Appl. No. 11/436,585, 9 pages.
Gelbart et al., "Method and Device for Closing Holes in Tissue," Amendment filed Oct. 26, 2009, for U.S. Appl. No. 11/436,585, 13 pages.
International Search Report, mailed Jan. 8, 2007, for PCT/CA2006/001123, 5 pages.
International Search Report, mailed Sep. 4, 2009, for PCT/US2009/043612, 7 pages.
Jatene, "Left Ventricular Aneurysmectomy," *Journal of Thoracic and Cardiovascular Surgery* 89(3):321-331, 1985.
Konings et al., "Development of an Intravascular Impedance Catheter for Detection of Fatty Lesions in Arteries," *IEEE Transactions on Medical Imaging*, 16(4):439-446, 1997.
Lichtenstein, "Method and Apparatus for Percutaneous Reduction of Anterior-Posterior Diameter of Mitral Valve," U.S. Appl. No. 10/690,131, filed Oct. 20, 2003, 31 pages.
Lichtenstein, "Method and Apparatus for Percutaneous Reduction of Anterior-Posterior Diameter of Mitral Valve," Office Action mailed May 15, 2006, for U.S. Appl. No. 10/690,131, 9 pages.
Lichtenstein, "Method and Apparatus for Percutaneous Reduction of Anterior-Posterior Diameter of Mitral Valve," U.S. Appl. No. 11/400,260, filed Apr. 10, 2006, 32 pages.
Lichtenstein, "Method and Apparatus for Percutaneous Reduction of Anterior-Posterior Diameter of Mitral Valve," Office Action mailed Dec. 1, 2008, for U.S. Appl. No. 11/400,260, 10 pages.
Lichtenstein et al., "Method for Anchoring a Mitral Valve," U.S. Appl. No. 11/475,978, filed Jun. 28, 2006, 15 pages.
Lichtenstein et al., "Method for Anchoring a Mitral Valve," Office Action mailed May 1, 2009, for U.S. Appl. No. 11/475,978, 6 pages.
Lichtenstein et al, "Method for Anchoring a Mitral Valve," Amendment filed Aug. 31, 2009, for U.S. Appl. No. 11/475,978, 24 pages.
Lichtenstein et al, "Method for Anchoring a Mitral Valve," Office Action mailed Dec. 29, 2009, for U.S. Appl. No. 11/475,978, 7 pages.
Lichtenstein et al, "Method for Anchoring a Mitral Valve," Amendment filed Mar. 26, 2010, for U.S. Appl. No. 11/475,978, 26 pages.
Lichtenstein et al., "System for Improving Diastolic Dysfunction," U.S. Appl. No. 11/497,309, filed Aug. 2, 2006, 13 pages.
Mack, "New Techniques for Percutaneous Repair of the Mitral Valve," *Heart Failure Review*, 11:259-268, 2006.
Menicanti et al., "The Dor Procedure: What has Changed After Fifteen Years of Clinical Practice?" *Journal of Thoracic and Cardiovascular Surgery* 124(5):886-890, Nov. 2002.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Rivera et al., "Ventricular Aneurysms and Akinesis," *Cleveland Clinic Quarterly* 45(1):133-135, 1978.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.

Timek et al., "Septal-Lateral Annular Cinching Abolishes Acute Ischemic Mitral Regurgitation," *Journal of Thoracic and Cardiovascular Surgery*, 123(5):881-888, 2002.
Torrent-Guasp et al., "Spatial Orientation of the Ventricular Muscle Band and Approach to Partial Ventriculotomy in Heart Failure," *Pathogenesis and Treatment*, Ch. 36, pp. 685-693.
Valvano et al., "Thermal Conductivity and Diffusivity of Biomaterials Measured with Self-Heated Thermistors," *International Journal of Thermodynamics*, 6(3):301-311, 1985.
Written Opinion, mailed Jan. 8, 2007, for PCT/CA2006/001123, 6 pages.
Written Opinion, mailed Sep. 4, 2009, for PCT/US2009/043612, 6 pages.
Lichtenstein et al., "System for Improving Diastolic Dysfunction," Office Action mailed Dec. 24, 2008 for U.S. Appl. No. 11/497,309, 8 pages.
Lichtenstein et al., "System for Improving Diastolic Dysfunction," Amendment filed Apr. 22, 2009 for U.S. Appl. No. 11/497,309, 23 pages.
Lichtenstein et al., "System for Improving Diastolic Dysfunction," Office Action mailed Aug. 5, 2009 for U.S. Appl. No. 11/497,309, 10 pages.
Lichtenstein et al., "System for Improving Diastolic Dysfunction," Amendment filed Oct. 23, 2009 for U.S. Appl. No. 11/497,309, 9 pages.
Lichtenstein et al., "System for Improving Diastolic Dysfunction," Office Action mailed Jan. 20, 2010 for U.S. Appl. No. 11/497,309, 10 pages.
Lichtenstein et al., "System for Improving Diastolic Dysfunction," Amendment filed Apr. 7, 2010 for U.S. Appl. No. 11/497,309, 8 pages.
Gelbart et al., "Artificial Valve," Office Action mailed May 7, 2010 for U.S. Appl. No. 11/497,306, 12 pages.
Gelbart et al., "Artificial Valve," Amendment filed Jan. 29, 2010 for U.S. Appl. No. 11/497,306, 22 pages.
Gelbart et al., "Method and Device for Closing Holes in Tissue," Office Action mailed Feb. 23, 2012 for U.S. Appl. No. 12/777,883, 8 pages.
Gelbart et al., "Method and Device for Closing Holes in Tissue," Amendment filed May 4, 2012 for U.S. Appl. No. 12/777,883, 12 pages.
Becker, R. et al., "Ablation of Atrial Fibrillation: Energy Sources and Navigation Tools: A Review," *Journal of Electrocardiology*, 37(Supplement 2004):55-62, 2004.
Calkins, Hugh, "Radiofrequency Catheter Ablation of Supraventricular Arrhythmias," *Heart*, 85:594-600, 2001.
Dahlgren et al., "System for Mechanical Adjustment of Medical Implants," Office Action mailed Oct. 5, 2009 for U.S. Appl. No. 11/902,099, 11 pages.
Dahlgren et al., "System for Mechanical Adjustment of Medical Implants," Amendment filed Apr. 2, 2010 for U.S. Appl. No. 11/902,099, 19 pages.
Dahlgren et al., "System for Mechanical Adjustment of Medical Implants," Office Action mailed Jul. 8, 2010 for U.S. Appl. No. 11/902,099, 7 pages.
Dahlgren et al., "System for Mechanical Adjustment of Medical Implants," Amendment filed Nov. 1, 2010 for U.S. Appl. No. 11/902,099, 12 pages.
De Ponti et al., "Non-Fluoroscopic Mapping Systems for Electrophysiology: The 'Tool or Toy' Dilemma After 10 Years," *European Heart Journal* 27:1134-1136, 2006.
European Search Report, mailed Jun. 26, 2008, for EP 08100878.1, 11 pages.
Gabriel et al., "The Dielectric Properties of Biological Tissues: I. Literature Survey," *Phys. Med. Biol.* 41:2231-2249, 1996.
Gelbart, "System for Implanting a Microstimulator," Office Action mailed Aug. 20, 2009 for U.S. Appl. No. 12/068,878, 11 pages.
Gelbart, "System for Implanting a Microstimulator," Amendment filed Jan. 20, 2010 for U.S. Appl. No. 12/068,878, 26 pages.
Gelbart, "System for Implanting a Microstimulator," Office Action mailed Aug. 18, 2010 for U.S. Appl. No. 12/068,878, 11 pages.
Gelbart et al., "Automatic Atherectomy System," Office Action mailed Jun. 15, 2011, for U.S. Appl. No. 12/950,871, 16 pages.

(56) References Cited

OTHER PUBLICATIONS

Gelbart et al., "Automatic Atherectomy System," Amendment filed Aug. 4, 2009 for U.S. Appl. No. 11/436,584, 35 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Amendment filed Sep. 15, 2011 for U.S. Appl. No. 12/950,871, 21 pages.
Gelbart et al., "Automatic Atherectomy System," Office Action mailed Mar. 4, 2009 for U.S. Appl. No. 11/436,584, 7 pages.
Gelbart et al., "Automatic Atherectomy System," Office Action mailed Dec. 1, 2009 for U.S. Appl. No. 11/436,584, 10 pages.
Gelbart et al., "Automatic Atherectomy System," Office Action mailed Dec. 14, 2010 for U.S. Appl. No. 11/436,584, 12 pages.
Gelbart et al., "Automatic Atherectomy System," Office Action mailed Sep. 25, 2012 for U.S. Appl. No. 13/404,834, 8 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Amendment filed Aug. 16, 2010 for U.S. Appl. No. 11/475,950, 22 pages.
Gelbart et al., "Intra-Cardiac Mapping and Ablation Method," Amendment filed Feb. 23, 2011 for U.S. Appl. No. 11/475,950, 28 pages.
Gelbart et al., "Intra-Cardiac Mapping and Ablation Method," Office Action mailed Jun. 23, 2010 for U.S. Appl. No. 11/475,950, 18 pages.
Gelbart et al., "Intra-Cardiac Mapping and Ablation Method," Office Action mailed Nov. 23, 2010 for U.S. Appl. No. 11/475,950, 25 pages.
Gelbart et al., "Intra-Cardiac Mapping and Ablation Method," Preliminary Amendment filed Aug. 29, 2007 for U.S. Appl. No. 11/475,950, 42 pages.
Gelbart et al., "Liposuction System," Office Action mailed Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.
Gelbart et al., "Liposuction System," Office Action mailed Sep. 14, 2011 for U.S. Appl. No. 12/010,458, 9 pages.
Gelbart et al., "Liposuction System," Amendment filed Dec. 7, 2011 for U.S. Appl. No. 12/010,458, 15 pages.
Gelbart et al., "Medical Device for Use in Bodily Lumens, for Example an Atrium," Office Action mailed Jul. 25, 2011 for U.S. Appl. No. 11/941,819, 9 pages.
International Preliminary Report on Patentability, issued Jan. 6, 2009, for PCT/US2007/014902, 8 pages.
International Search Report, mailed Dec. 6, 2004, for PCT/IB2004/002581, 3 pages.
International Search Report, mailed Dec. 2, 2009, for PCT/US2008/083644, 4 pages.
International Search Report, mailed Dec. 5, 2007, for PCT/US2007/014902, 4 pages.
International Search Report, mailed Sep. 10, 2010, for PCT/US2010/021835, 4 pages.
Jaramillo et al., "Surgical Instrument and Method for Tensioning and Securing a Flexible Structure," Office Action mailed Dec. 13, 2010 for U.S. Appl. No. 12/246,614, 12 pages.
Jaramillo et al., "Surgical Instrument and Method for Tensioning and Securing a Flexible Structure," Amendment filed Mar. 14, 2011 for U.S. Appl. No. 12/246,614, 22 pages.
Jaramillo et al., "Surgical Instrument and Method for Tensioning and Securing a Flexible Structure," Office Action mailed May 27, 2011 for U.S. Appl. No. 12/246,614, 23 pages.
Jaramillo et al., "Surgical Instrument and Method for Tensioning and Securing a Flexible Structure," Office Action mailed Jul. 8, 2011 for U.S. Appl. No. 12/436,926, 13 pages.
Jaramillo et al., "Surgical Instrument and Method for Tensioning and Securing a Flexible Structure," Amendment filed Jul. 26, 2011 for U.S. Appl. No. 12/246,614, 41 pages.
Jaramillo et al., "Surgical Instrument and Method for Tensioning and Securing a Flexible Structure," Amendment filed Oct. 5, 2011 for U.S. Appl. No. 12/436,926, 32 pages.
Jaramillo et al., "Surgical Instrument and Method for Tensioning and Securing a Flexible Structure," Office Action mailed Jan. 11, 2012 for U.S. Appl. No. 12/436,926, 21 pages.
Jaramillo et al., "Surgical Instrument and Method for Tensioning and Securing a Flexible Structure," Amendment filed Feb. 27, 2012 for U.S. Appl. No. 12/436,926, 25 pages.
Jaramillo et al., "Surgical Instrument and Method for Tensioning and Securing a Flexible Structure," Office Action mailed Sep. 21, 2012 for U.S. Appl. No. 12/436,926, 14 pages.
Jaramillo et al., "Surgical Instrument and Method for Tensioning and Securing a Flexible Structure," Amendment filed Dec. 4, 2012 for U.S. Appl. No. 12/439,926, 19 pages.
Lichtenstein, "Methods and Devices for Altering Blood Flow Through the Left Ventricle," Preliminary Amendment mailed Mar. 6, 2006 for U.S. Appl. No. 10/571,165, 7 pages.
Lichtenstein, "Methods and Devices for Altering Blood Flow Through the Left Ventricle," Office Action mailed Mar. 26, 2007 for U.S. Appl. No. 10/622,129, 17 pages.
Lichtenstein, "Methods and Devices for Altering Blood Flow Through the Left Ventricle," Amendment mailed Jul. 26, 2007 for U.S. Appl. No. 10/622,129, 17 pages.
Lichtenstein, "Methods and Devices for Altering Blood Flow Through the Left Ventricle," Office Action mailed Nov. 14, 2007 for U.S. Appl. No. 10/622,129, 6 pages.
Lichtenstein, "Methods and Devices for Altering Blood Flow Through the Left Ventricle," Preliminary Amendment mailed Feb. 14, 2008 for U.S. Appl. No. 10/622,129, 15 pages.
Lichtenstein, "Methods and Devices for Altering Blood Flow Through the Left Ventricle," Examiner's Amendment mailed Mar. 2, 2009 for U.S. Appl. No. 10/622,129, 5 pages.
Lichtenstein, "Methods and Devices for Altering the Blood Flow Through the Left Ventricle," Office Action mailed Jul. 9, 2010 for U.S. Appl. No. 10/571,165, 8 pages.
Lichtenstein et al., "System for Improving Diastolic Dysfuntion," Preliminary Amendment filed Oct. 14, 2010 for U.S. Appl. No. 12/904,885, 22 pages.
Lichtenstein et al., "System for Improving Diastolic Dysfunction," Office Action mailed Sep. 18, 2012 for U.S. Appl. No. 12/904,885, 15 pages.
Lopes et al., "Enhanced Medical Device for Use in Bodily Cavities, for Example an Atrium," U.S. Appl. No. 61/435,213, filed Jan. 21, 2011, 320 pages.
Lopes et al., "Enhanced Medical Device for Use in Bodily Cavities, for Example an Atrium," U.S. Appl. No. 61/485,987, filed May 13, 2011, 401 pages.
Lopes et al., Enhanced Medical Device for Use in Bodily Cavities, for Example an Atrium, U.S. Appl. No. 61/488,639, filed May 20, 2011, 434 pages.
Lopes et al., Enhanced Medical Device for Use in Bodily Cavities, for Example an Atrium, U.S. Appl. No. 61/515,141, filed Aug. 8, 2011, 508 pages.
Tegzes, "Medical Kit for Constricting Tissue or a Bodily Orifice, for Example, a Mitral Valve," U.S. Appl. No. 61/467,883, filed Mar. 25, 2011, 167 pages.
Written Opinion, mailed Dec. 2, 2009, for PCT/US2008/083644, 9 pages.
Written Opinion, mailed Dec. 5, 2007, for PCT/US2007/014902, 7 pages.
Written Opinion, mailed Sep. 10, 2010, for PCT/US2010/021835, 6 pages.
Written Opinion, mailed Jun. 16, 2011, for PCT/US2010/050945, 4 pages.
Gelbart et al., "Method and Device for Closing Holes in Tissue", Office Action mailed Nov. 20, 2014 for U.S. Appl. No. 13/652,299, 9 pages.
Goertzen et al., "Tissue Anchor System", Notice of Allowance mailed Dec. 3, 2014 for U.S. Appl. No. 13/247,380, 14 pgs.

(56) References Cited

OTHER PUBLICATIONS

Tegzes, "Medical Kit for Constricting Tissue or a Bodily Orifice, for Example, a Mitral Valve", Amendment filed Dec. 3, 2014 for U.S. Appl. No. 13/421,677, 17 pgs.
Dahlgren et al., "Medical Device, Kit and Method for Constricting Tissue or a Bodily Orifice, for Example, a Mitral Valve", Amendment filed Dec. 30, 2014 for U.S. Appl. No. 13/917,469, 18 pgs.
Dahlgren et al., "Medical Device, Kit and Method for Constricting Tissue or a Bodily Orifice, for Example, a Mitral Valve", Office Action mailed Mar. 5, 2015 for U.S. Appl. No. 13/917,469, 52 pgs.
Gelbart et al., "Method and Device for Closing Holes in Tissue", Amendment filed Feb. 5, 2015 for U.S. Appl. No. 13/652,299, 11 pages.
Lichtenstein et al., "System for Improving Diastolic Dysfunction", Office Action mailed Apr. 10, 2015 for U.S. Appl. No. 12/904,885, 67 pages.
Biotronik'S "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Lichtenstein et al., "Method for Anchoring a Mitral Valve", Office Action mailed Apr. 24, 2015 for co-pending U.S. Appl. No. 14/162,469, 61 pages.
Lichtenstein et al., "Method for Anchoring a Mitral Valve", Amendment filed Jun. 30, 2015 for U.S. Appl. No. 14/162,469, 7 pages.
Dahlgren et al., "Medical Device, Kit and Method for Constricting Tissue or a Bodily Orifice, for Example, a Mitral Valve", Amendment filed Jun. 4, 2015 for U.S. Appl. No. 13/917,469, 17 pgs.
Lichtenstein et al., "System for Improving Diastolic Dysfunction", Amendment filed Aug. 10, 2015 for U.S. Appl. No. 12/904,885, 18 pgs.
Gelbart et al., "Method and Device for Closing Holes in Tissue", Amendment filed Aug. 14, 2015 for U.S. Appl. No. 13/652,299, 16 pages.
Gelbart et al., "Method and Device for Closing Holes in Tissue", Office Action mailed Nov. 4, 2015 for U.S. Appl. No. 13/652,299, 12 pages.
Lichtenstein et al., "System for Improving Diastolic Dysfunction", Final Office Action mailed Nov. 23, 2015 for U.S. Appl. No. 12/904,885, 43 pages.
Extended European Search Report mailed Sep. 18, 2014 for EP 10821276.2, 10 pages.
Gelbart et al., "Automatic Atherectomy System", Notice of Allowance mailed May 10, 2013 and Certificate of Correction mailed May 6, 2014 for U.S. Appl. No. 13/404,834, 11 pgs.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance mailed Aug. 20, 2010 for U.S. Appl. No. 11/436,584, 12 pgs.
Gelbart et al., "Automatic Atherectomy System", Notice of Allowance mailed Nov. 25, 2011 and Certificate of Correction mailed Jul. 17, 2012 for U.S. Appl. No. 12/950,871, 24 pgs.
Gelbart et al., "Method and Device for Closing Holes in Tissue", Response to Quayle Action filed Jul. 14, 2014 for U.S. Appl. No. 13/652,299, 29 pages.
Gelbart et al., "Method and Device for Closing Holes in Tissue", Quayle Action mailed May 20, 2014 for U.S. Appl. No. 13/652,299, 25 pages.
Gelbart et al., "Method and Device for Closing Holes in Tissue", Preliminary Amendment fiiled Feb. 21, 2013 for U.S. Appl. No. 13/652,299, 9 pages.
Gelbart et al., "Method and Device for Closing Holes in Tissue", Notice of Allowance mailed Feb. 24, 2010, Supplemental Notice of Allowance mailed Mar. 24, 2010 and Remarks filed after allowance on Apr. 9, 2010 for U.S. Appl. No. 11/436,585, 20 pgs.
Gelbart et al., "Method and Device for Closing Holes in Tissue", Notice of Allowance mailed Aug. 22, 2012 for U.S. Appl. No. 12/777,883, 12 pgs.
Goertzen et al., "Tissue Anchor System", Notice of Allowance mailed Jul. 7, 2014 for U.S. Appl. No. 13/247,380, 8 pgs.
Goertzen et al., "Tissue Anchor System", Notice of Allowance mailed Oct. 16, 2014 for U.S. Appl. No. 13/247,380, 41 pgs.
Lichtenstein et al., "Method for Anchoring a Mitral Valve", Notices of Allowance mailed Oct. 2, 2013 and Nov. 13, 2013 for U.S. Appl. No. 13/872,870, 35 pgs.
Lichtenstein et al., "Method for Anchoring a Mitral Valve", Notice of Allowance mailed Jan. 28, 2013 for U.S. Appl. No. 11/475,978, 24 pgs.
Lichtenstein et al., "Method for Anchoring a Mitral Valve", Preliminary Amendment filed Jan. 24, 2014 for U.S. Appl. No. 14/162,469, 9 pgs.
Lichtenstein et al., "System for Improving Diastolic Dysfunction", Notice of Allowance mailed Jul. 12, 2010 for U.S. Appl. No. 11/497,309, 8 pgs.
Lichtenstein et al., "System for Improving Diastolic Dysfunction", Office Action mailed Jan. 29, 2014 for U.S. Appl. No. 12/904,885, 38 pgs.
Lichtenstein et al., "System for Improving Diastolic Dysfunction", Amendment filed Apr. 9, 2014 for U.S. Appl. No. 12/904,885, 24 pgs.
Lichtenstein et al., "System for Improving Diastolic Dysfunction", Amendment filed Dec. 18, 2012 for U.S. Appl. No. 12/904,885, 23 pgs.
"Constellation Mapping Catheters", Brochure, Boston Scientific Corp., 2 pgs, ©2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, ©Biosense Webster, Inc. 2009 All rights reserved. 1109003.0.
Biotronik'S "AlCath Flutter Gold Cath for Atrial Flutter Available in EU", medGadget, 3 pgs, http://www.medgadget. com/2013/09/biotroniks-alcath-flutter-gold-cath-for-atrial-flutter-unveiled-in-europe.html[Jun. 24, 2014 2:37:09 PM].
Dahlgren et al., "Medical Device, Kit and Method for Constricting Tissue or a Bodily Orifice, For Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, For Example a Mitral Valve", Final Office Action mailed Feb. 13, 2013 for U.S. Appl. No. 12/894,912, 35 pgs.
Dahlgren et al., "Medical Device, Kit and Method for Constricting Tissue or a Bodily Orifice, For Example a Mitral Valve", Office Action mailed Aug. 30, 2012 for U.S. Appl. No. 12/894,912, 16 pgs.
Dahlgren et al., "Medical Device, Kit and Method for Constricting Tissue or a Bodily Orifice, For Example a Mitral Valve", Response filed Jun. 13, 2013 for U.S. Appl. No. 121894,912, 3 pgs.
Dahlgren et al., "Medical Device, Kit and Method for Constricting Tissue or a Bodily Orifice, for Example, a Mitral Valve", Office Action mailed Jul. 9, 2014 for U.S. Appl. No. 131917,469, 37 pgs.
Goertzen et al., "Tissue Anchor System", Amendment filed Apr. 29, 2013 for U.S. Appl. No. 13/247,380, 22 pgs.
Goertzen et al., "Tissue Anchor System", Amendment filed Dec. 10, 2013 for U.S. Appl. No. 13/247,380, 11 pgs.
Goertzen et al., "Tissue Anchor System", Amendment filed Oct. 11, 2013 for U.S. Appl. No. 13/247,380, 10 pgs.
Goertzen et al., "Tissue Anchor System", Office Action mailed Aug. 13, 2013 for U.S. Appl. No. 13/247,380, 15 pgs.
Goertzen et al., "Tissue Anchor System", Office Action mailed Jan. 29, 2013 for U.S. Appl. No. 13/247,380, 10 pgs.
International Search Report mailed Jun. 16, 2011 for PCT/US2010/050945, 5 pgs.
Lichtenstein "Closing Openings in Anatomical Tissue", Amendment filed Aug. 8, 2013 for U.S. Appl. No. 13/112,695, 23 pgs.
Lichtenstein "Closing Openings in Anatomical Tissue", Office Action mailed May 8, 2013 for U.S. Appl. No. 13/112,695, 12 pgs.
Lichtenstein, "Closing Openings in Anatomical Tissue", Final Office Action mailed Dec. 4, 2013 for U.S. Appl. No. 13/112,695, 31 pages.
Mazur et al., "Bone Fixation Device, Tools and Methods", U.S. Appl. No. 61/138,920, filed Dec. 18, 2008, 88 pgs.

(56) References Cited

OTHER PUBLICATIONS

Star Closure System Brochure, 2005, Abbott Vascular, pp. 1-4.
Tegzes, "Medical Kit for Constricting Tissue or a Bodily Orifice, for Example, a Mitral Valve", Office Action mailed Jul. 11, 2014 for U.S. Appl. No. 13/421,677, 9 pgs.
Written Opinion mailed Dec. 6, 2004 for PCT/IB2004/002581, 8 pgs.
Gelbart et al., "Method and Device for Closing Holes in Tissue", Office Action mailed May 14, 2015 for U.S. Appl. No. 13/652,299, 67 pages.
Amendment filed in co-pending U.S. Appl. No. 13/652,299 on Sep. 30, 2016.
Notice of Allowance issued in co-pending U.S. Appl. No. 13/652,299 mailed Oct. 28, 2016.
Amendment filed in co-pending U.S. Appl. No. 12/904,885 on Nov. 17, 2016.
Office Action issued in co-pending U.S. Appl. No. 14/955,544 mailed Mar. 21, 2017.

\* cited by examiner

MEDICAL DEVICE FOR CONSTRICTING TISSUE OR A BODILY ORIFICE, FOR EXAMPLE A MITRAL VALVE

CROSS-REFERENCE TO RELATED APPLICATION

This application is a division of U.S. patent application Ser. No. 12/120,195, filed May 13, 2008, now pending, which is incorporated herein, by reference, in its entirety.

BACKGROUND

1. Field

This disclosure is generally related to percutaneous or minimally invasive surgery, and more particularly to percutaneously deployed medical devices suitable for constricting tissue or a bodily orifice such as a mitral valve 2. Description of the Related Art Cardiac surgery was initially undertaken only by performing a sternotomy, a type of incision in the center of the chest, which separates the sternum (chest bone) to allow access to the heart. In the previous several decades, more and more cardiac operations are performed using a percutaneous technique, which is a medical procedure where access to inner organs or other tissue is gained via a catheter.

Percutaneous surgeries benefit patients by reducing surgery risk, complications, and recovery time. However, the use of percutaneous technologies also raises some particular challenges. Medical devices used in percutaneous surgery need to be deployed via narrow tubes called catheter sheaths, which significantly increase the complexity of the device structure. As well, doctors do not have direct visual contact with the medical tools used once they are placed within the body, and positioning the tools correctly and operating the tools successfully can often be very challenging.

One example of where percutaneous medical techniques are starting to be used is in the treatment of a heart disorder called mitral regurgitation. Mitral regurgitation is a condition in which blood flows backward from the left ventricle into the left atrium. The mitral apparatus is made up of four major structural components and includes the annulus, the two leaflets, the chordae and the papillary muscles. Improper function of any one of these structures or in combination can lead to mitral regurgitation. Annular dilation is a major component in the pathology of mitral regurgitation regardless of causes and is manifested in mitral regurgitation related to dilated cardiomyopathy and chronic mitral regurgitation due to ischemia.

The mitral valve is intended to prevent the undesired flow of blood from the left ventricle into the left atrium when the left ventricle contracts. In a normal mitral valve, the geometry of the mitral valve ensures the cusps overlay each other to preclude the regurgitation of blood during left ventricular contraction and thereby prevent elevation of pulmonary vascular pressures and resultant symptoms of shortness of breath. Studies of the natural history of mitral regurgitation have found that totally asymptomatic patients with severe mitral insufficiency usually progress to severe disability within 5 years.

At present treatment consists of either mitral valve replacement or repair. Both methods require open heart surgery. Replacement can be performed with either mechanical or biological valves and is particularly suitable when one of the mitral cusps has been severely damaged or deformed. The mechanical valve carries the risk of thromboembolism and requires anticoagulation with all of its potential hazards, whereas the biological prosthesis suffers from limited durability. Another hazard with replacement is the risk of endocarditis. These risks and other valve related complications are greatly diminished with valve repair. Mitral valve repair is theoretically possible if the mitral valve leaflets are structurally normal but fail to appropriately coapt because of annular dilatation and/or papillary muscle dysfunction. Various surgical procedures have been developed to improve coaptation of the leaflet and to correct the deformation of the mitral valve annulus and retain the intact natural heart valve function. These procedures generally involve reducing the circumference of the posterior mitral leaflet annulus (lateral annulus) where most of the dilatation occurs. The annulus of the anterior leaflet (septal annulus) does not generally dilate because it is anchored to the fibrous skeleton at the base of the heart. Such techniques, known as mitral annuloplasty, typically suture a prosthesis around the base of the valve leaflets shortening the lateral annulus to reshape the mitral valve annulus and minimize further dilation. Different types of mitral annuloplasty prostheses have been developed for use in such surgery. In general, such prostheses are annular or partially annular shaped and may be formed from rigid or flexible material.

Mitral valve surgery requires an extremely invasive approach that includes a chest wall incision, cardiopulmonary bypass, cardiac and pulmonary arrest, and an incision on the heart itself to gain access to the mitral valve. Such a procedure is expensive, requires considerable time, and is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction. Furthermore, the effectiveness of such procedures is difficult to assess during the procedure and may not be known until a much later time. Hence, the ability to make adjustments to or changes in the prosthesis function to obtain optimum effectiveness is extremely limited. Correction at a later date would require another open heart procedure.

In an attempt to treat mitral regurgitation without the need for cardiopulmonary bypass and without opening the chest, percutaneous approaches have been devised to repair the valve or place a correcting apparatus for correcting the annulus relaxation. Such approaches make use of devices which can be generally grouped into two types:

devices deforming (mainly shortening) the coronary sinus devices pulling together two anchor points in order to affect the mitral valve, one of the anchor points can be the coronary sinus (typically using a wire that is pulled and secured).

Neither approach emulates the current "gold standard" in mitral valve repair annuloplasty using a ring the completely encircles the mitral valve. Both approaches suffer from several problems as a result of attempting to reshape the mitral annulus using an alternative method. Devices that deform the coronary sinus, while suitable for percutaneous procedures, are not effective in controlling the leakage of the mitral valve as the forces are not applied from the correct opposite sides of the valve, which are the lateral annulus and the septal annulus. The prior art devices of the second type are not easily adapted to a percutaneous procedure. In order to achieve shortening in the direction connecting the lateral annulus to the septal annulus the anchor points have to be located along this line, so pulling them together will affect the desired direction of shortening. Pulling applied along a different direction will distort the mitral valve but will not achieve the optimal approximation of the two leaflets.

Thus, there is a need for methods and apparatus that enable the ability to create a full ring mitral annuloplasty via a percutaneous or intravascular procedure.

BRIEF SUMMARY OF THE INVENTION

The present design of a medical device with enhanced capabilities for percutaneous deployment and annulus cinching employs a superior method for constricting tissue or a bodily orifice, such as the mitral valve, tricuspid valve, or aortic valve. The device may employ methods that enable a complete ring to be anchored to tissue and may enable reduction of the circumference of said ring during installation or at a later time. Reference throughout this specification is made to cardiac surgery, but the invention may also be used in gastric surgery, bowel surgery, or other surgeries in which tissue may be drawn together. The invention may also be used to draw or hold tissue not part of an orifice or annulus together. The invention may be used in minimally invasive surgery as well as intravascular or percutaneous surgery. Other advantages will become apparent from the teaching herein to those of skill in the art.

At least one embodiment may be summarized as a method of constricting tissue or a bodily orifice or cavity, the method comprising delivering a plurality of anchors to the tissue or bodily orifice or cavity intravascularly; implanting the plurality of anchors; connecting the plurality of anchors by at least one joining member; and contracting at least one joining member.

The method may further include constricting a bodily orifice that is a mitral valve. The method may further include a flexible cable as the joining member. The anchors may comprise a helical portion or multiple barbs. The method may further include guiding the plurality of anchors to implant sites by means of at least one guide rail. The plurality of anchors may be released proximate to a change in curvature of the guide rail. Guide rails may be connected at distal tips.

At least one embodiment may be summarized as a medical system for constricting an orifice including a device positionable in at least a portion of a bodily organ; a plurality of guide rails; a plurality of anchors releasably guided by said guide rails; at least one structure used to locate said guide rails; means of connecting said anchors and a means of shortening or bending said connecting means.

The system may be deployed intravascularly. The medical system may be positionable in a left atrium of a heart. The system may further include a plurality of anchors that are released proximate to a change in curvature of said guide rails. The plurality of anchors may be held captive within a cap prior to deployment. The plurality of anchors may be restricted from release from guide rails or other restraining member until anchors are implanted into tissue. The system may further include a means of connecting anchors by a member that is shortened by application of an external magnetic field. The medical system may be foldable into a catheter.

At least one embodiment may be summarized as a medical system for attaching a flexible member to tissue including a flexible member attached to tissue by a plurality of anchors; said plurality of anchors guided by a plurality of rails; said anchors releasable proximate to a change in curvature of said rails; and a foldable frame configured to position said rails. The system may further be deliverable through a catheter. The flexible member may be adjusted after deployment. The system may further include a guiding frame with features for conforming to anatomical structures

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the claimed invention.

Overview of Device and Orifice Constriction Methods

Various embodiments of medical apparatus which are percutaneously or intravascularly deployed and may be used for constricting a bodily orifice are described herein.

Figure 1:
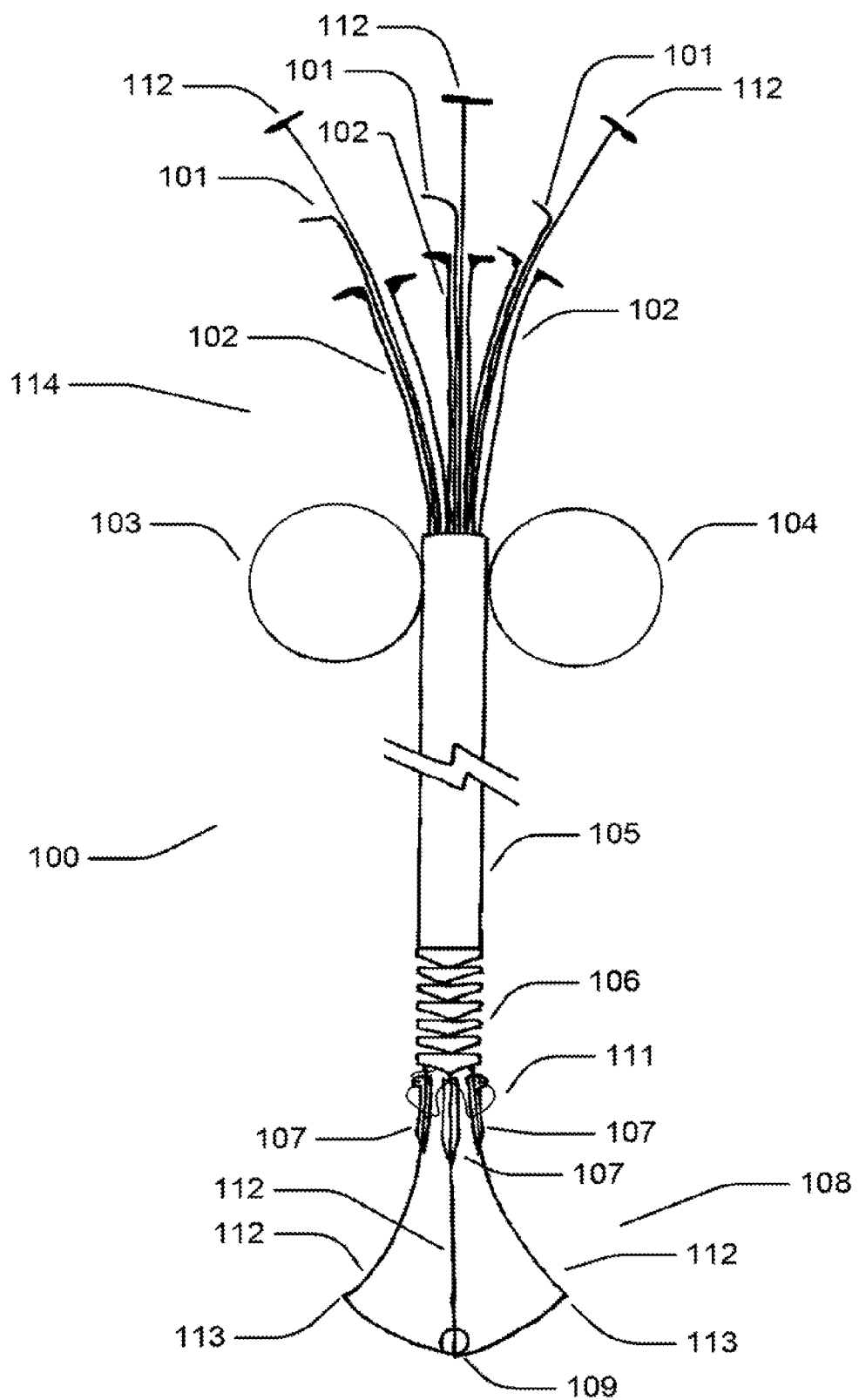
FIG. 1 is a schematic diagram of a treatment system according to one illustrated embodiment, including a medical device with a control handle, tissue anchors, and anchor guiding mechanism

FIG. 1 shows a medical device 100 according to one illustrated embodiment.

The medical device 100 may be used to deploy tissue anchors 107 and a flexible cable 111. The tissue anchors 107 may be secured to the annulus of an orifice and the flexible cable 111 may be used to constrict the orifice by pulling the anchors 107 inward. The medical device 100 comprises a flexible anchor guiding frame 108 that may be used to guide tissue anchors 107 to target positions on the orifice annulus. The anchor guiding frame may be made of a material such as Nitinol. The guiding frame 108 shown in FIG. 1 is comprised of three guide wires 112—one for each of the tissue anchors 107 shown. The guiding frame may include a different number of guide wires if more tissue anchors are desired. The guide wires 112 shown preferably have hinges 113 and may be connected with small loops 109. The hinges 113 and loops 109 enable the guiding frame to fold up to fit inside a catheter and to expand to extend across an orifice. Both the hinges 113 and loops 109 may be replaced by other mechanisms that enable bending. The medical device 100 typically has an articulating mechanism 106 that enables correctly orienting the anchor guiding mechanism during deployment of tissue anchors 107. The articulating mechanism 106 is preferably able to bend in any direction. The control knobs 103 and 104 may be used to control the bending of the articulating mechanism 106 using cables that are carried in the long flexible tube 105.

The medical device 100 shown comprises a long flexible tube 105 which extends from the articulating mechanism 106 to the medical device control mechanism 114 located at the proximal end of the catheter. Control mechanism 114 may consist of control knobs 103 and 104, release rods 101, push tubes 102, and guide wires 112. Additional controls may be required for other embodiments. The flexible tube 105 may have multiple lumens. Multi-lumen push tubes 102, guide wires 112, release rods 101, cable 111, and other mechanisms may be carried in flexible tube 105. In the embodiment given, each push tube 102 has two lumens. A guide wire 112 is carried in a first lumen and a release rod 101 is carried in a second lumen. Anchor s 107 are attached distal tips of release rods 101. The anchor 107 may be inserted into the annulus of an orifice by advancing the push tube 102 along the guide wire 112 and advancing or rotating the release rod 101 carried in the push tube 102 at the same rate. The anchor 107 may advance past the hinge 113 and embed into the annulus of the orifice to be constricted. Once the anchor 107 is embedded, the release rod 101 attached to the anchor may be retracted while the push tube 102 is held in place. Retraction of the release rod 101 causes the anchor 107 to detach from the distal tip of the release rod 101 and remain embedded in the tissue. Other embodiments may use different methods for releasing the tissue anchors 107.

Figure 2:
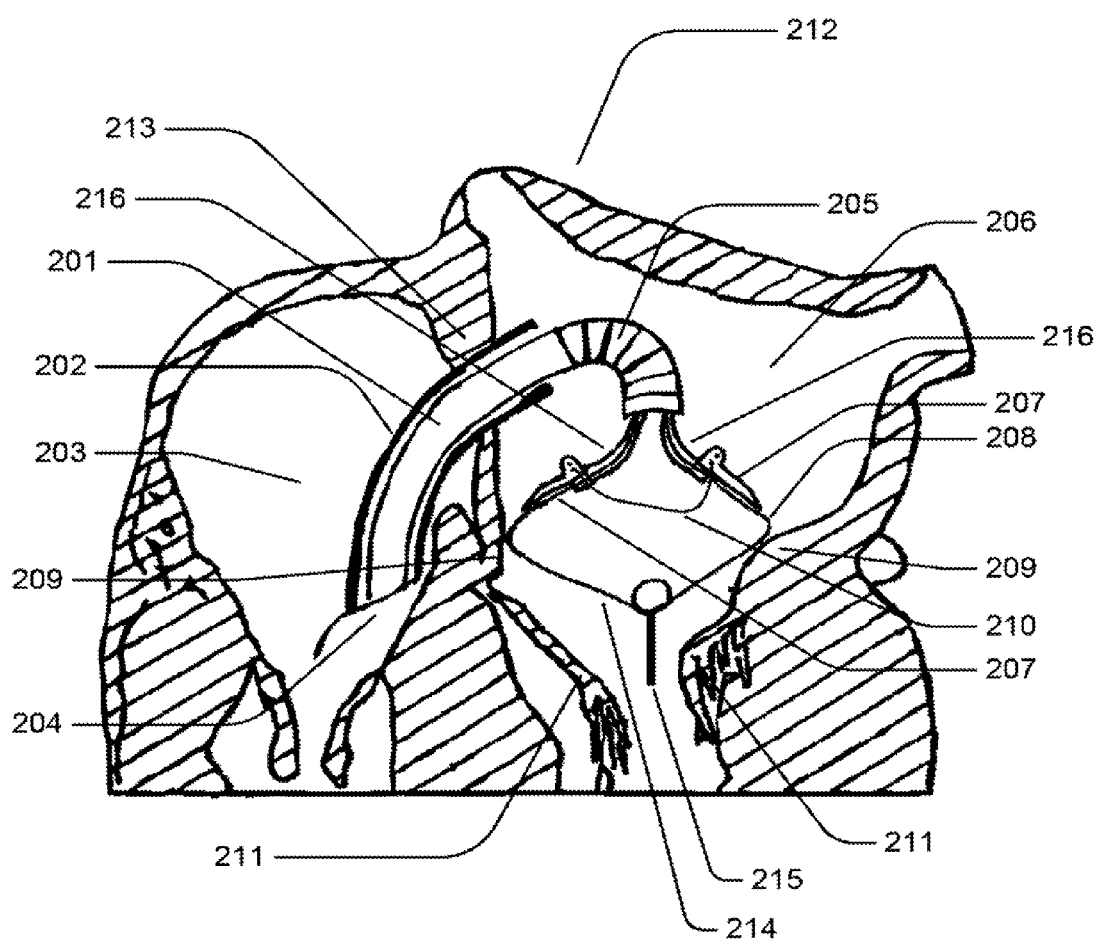
FIG. 2 is a cutaway diagram of a heart showing a medical device according to one illustrated embodiment percutaneously placed in a left atrium of the heart.

FIG. 2 shows a medical device useful in constricting a bodily orifice, for example a mitral valve, according to one illustrated embodiment.

The medical device may be percutaneously and/or intravascularly inserted into a portion of the heart 212, for example in a left atrium 206 of the heart 212. In this example, the medical device is delivered via a catheter 202 inserted via the inferior vena cava 204 and penetrating the transatrial septum 213 from a right atrium 203. The catheter 202 is preferably under 8 mm in diameter.

The flexible anchor guiding frame 214 expands after being delivered via the catheter 202 into a shape that preferably enables the tissue anchors 207 to be delivered to the desired position on the mitral annulus 209. The flexible anchor guiding frame 214 may be moved into the correct orientation by adjusting the shape of the articulating mechanism 205, advancing or retracting flexible tube 201, or rotating flexible tube 201. The flexible anchor guiding frame 214 preferably has an overall shape that enables said frame to take on a desired orientation within a cavity by conforming to the shape or being affected by the movement of anatomical features. Such a property is known as "self-locating". Minimal insertion force and operator guidance is typically needed to properly position the anchor guiding mechanism. The flexible anchor guiding frame 214 may also have specific features which cause it to orient correctly based on the position of an anatomical feature, such as the mitral valve leaflets 211. An example of such a feature is given by alignment fin 215. Alignment fin 215 is attached rigidly to flexible anchor guiding frame 214 and shaped so that it may be deflected to a particular orientation by an anatomical feature, such as mitral valve leaflets 211. As the flexible anchor guiding frame 214 is advanced toward an anatomical feature, such as the mitral valve annulus 209, the shape or motion of an anatomical feature, such as the mitral valve leaflets 211, may cause alignment fin 215, and thus attached flexible anchor guiding frame 214, to rotate or translate to a desired orientation or location.

The anchors 207 may be inserted into the annulus 209 by advancing the push tubes 216 along the guide wires 112. The anchors 207 may advance past the bend 208 and embed into the annulus 209. The embedded anchors 207 may then be released from the push tubes 216. The flexible cable 210 connecting the anchors 207 may then be tightened and secured to constrict the mitral annulus 209.

Figure 3:
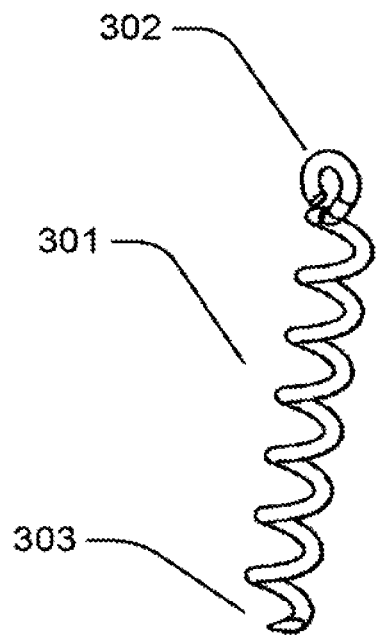
FIG. 3 is a diagram showing an example of a helical anchor.

FIG. 3 shows an example of a tissue anchor according to one illustrated embodiment. The helical tissue anchor 301 has a helical structure with sharp tip 303. Loop 302 may be used to connect to a mechanism for holding the tissue anchor 301 to a release rod. Loop 302 may also be used to attach tissue anchor 301 to a cable used for cinching the annulus of a bodily orifice.

Figure 4:
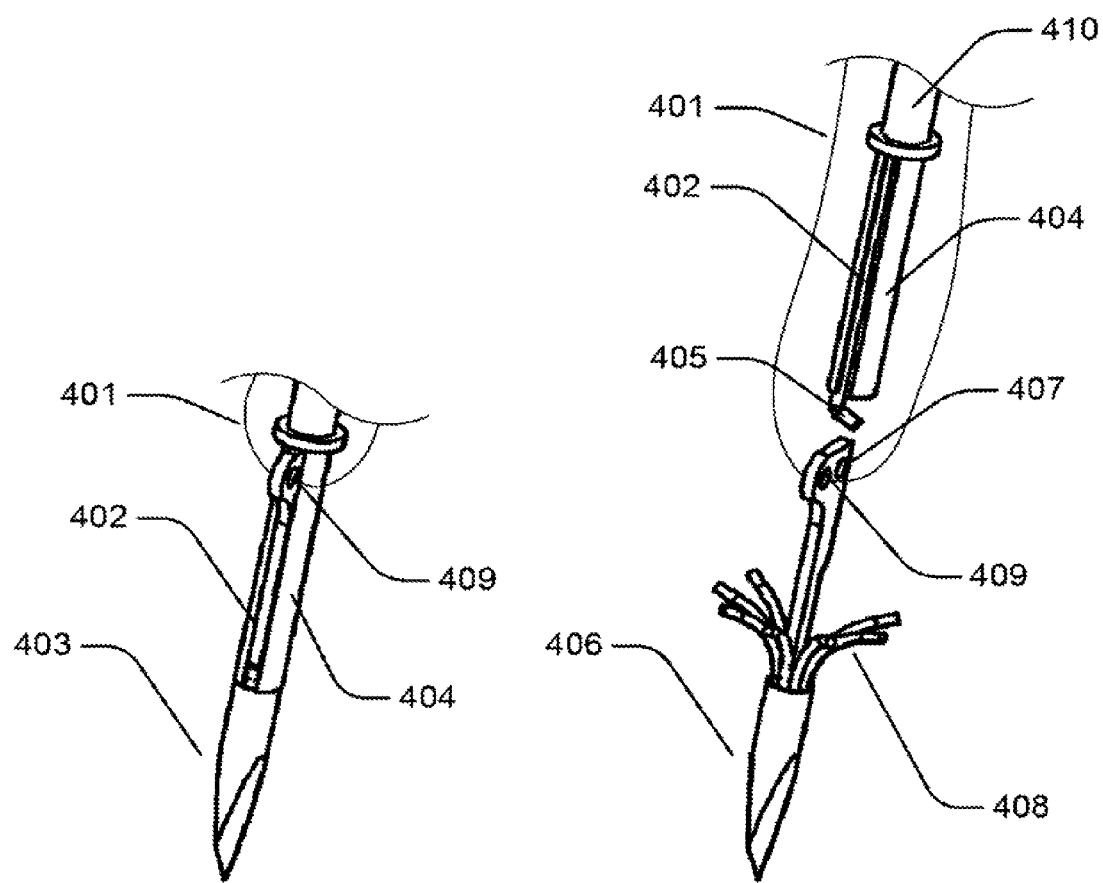
FIG. 4 is a diagram showing an example of a multi-barbed anchor that is encapsulated and an example of a multi-barbed anchor that is not encapsulated.

FIG. 4 shows an example of a tissue anchor according to one illustrated embodiment. Tissue anchor 403 is shown in a compressed configuration and tissue anchor 406 is shown in an expanded configuration. The tissue anchors 403, 406 comprise multiple barbs 408. The multiple barbs 408 may be compressed into constricting tube 404 as shown for tissue anchor 403. Compression of barbs 408 into constricting tube 404 enables the anchor to move more readily through a catheter and also to be inserted more readily into tissue.

Tissue anchor 403 may comprise a hole 409 that may be used to attach said anchor to a cable 401 used for cinching the annulus of a bodily orifice. Constricting tube 404 may comprise a slot 402 to allow anchor 403 to be ejected from constricting tube 404 in the case where hole 409 is mounted on a protruding flange.

Tissue anchor 406 may comprise a hole 407 that may be used to connect said anchor to release rod 405. Release rod 405 may be carried in a lumen of push tube 410. If constricting tube 404 is extended over hole 407 as shown for anchor 403, release rod 405 is held captive in hole 407 by the wall of tube 404. If constricting tube 404 is retracted to not cover hole 407, as shown for tissue anchor 406, release rod 405 is not held captive in hole 407 and said tissue anchor may become disconnected from constricting tube 404 and release rod 405.

Tissue anchor 406 may be disconnected from release rod 405 and barbs 408 may be uncompressed by retracting constricting tube 404 relative to the release rod 405 and tissue anchor 406. Retracting constricting tube 404 past the tips of barbs 408 causes said barbs to be released and expand. Retracting constricting tube 404 past hole 407 may release tissue anchor 406.

Figure 5:
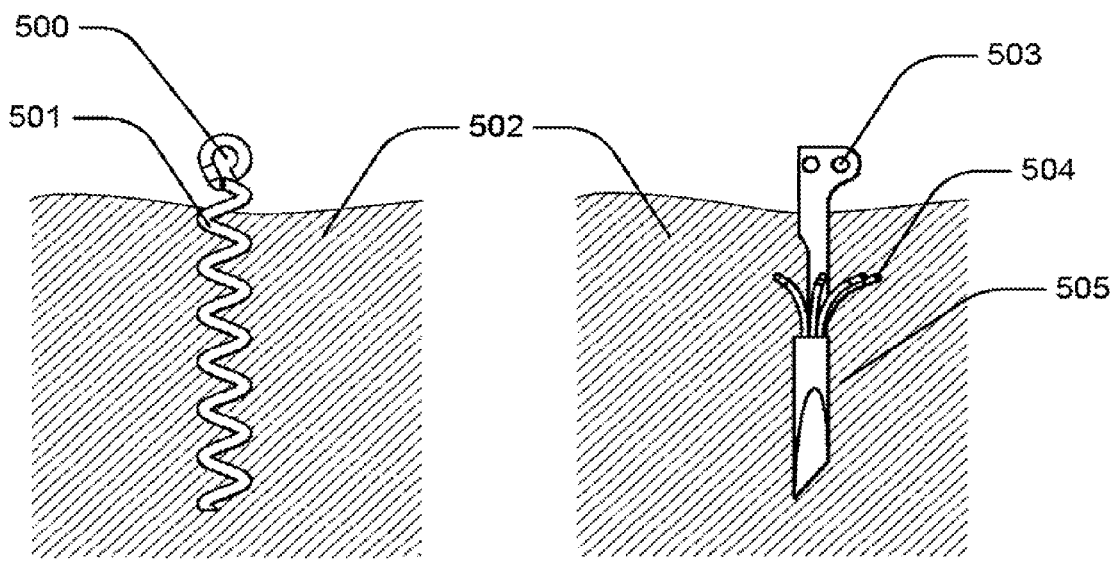
FIG. 5 is a diagram showing examples of helical anchors and barbed anchors embedded in tissue

FIG. 5 shows examples of tissue anchors embedded in tissue. Tissue anchor 501 is a helical anchor embedded in tissue 502. Tissue anchor 501 may include a loop 500. Tissue anchor 501 is embedded in tissue 502 by rotating said anchor. Tissue anchor 505 is a multi-barbed anchor embedded in tissue 502. Tissue anchor 505 may include a hole 503 that may be used to attach said tissue anchor to a cable used for cinching the annulus of a bodily orifice. Tissue anchor 505 is embedded in tissue 502 by pushing the anchor into the tissue. Barbs 504 provide resistance to restrict the tissue anchor 505 from being extracted.

Figure 6:
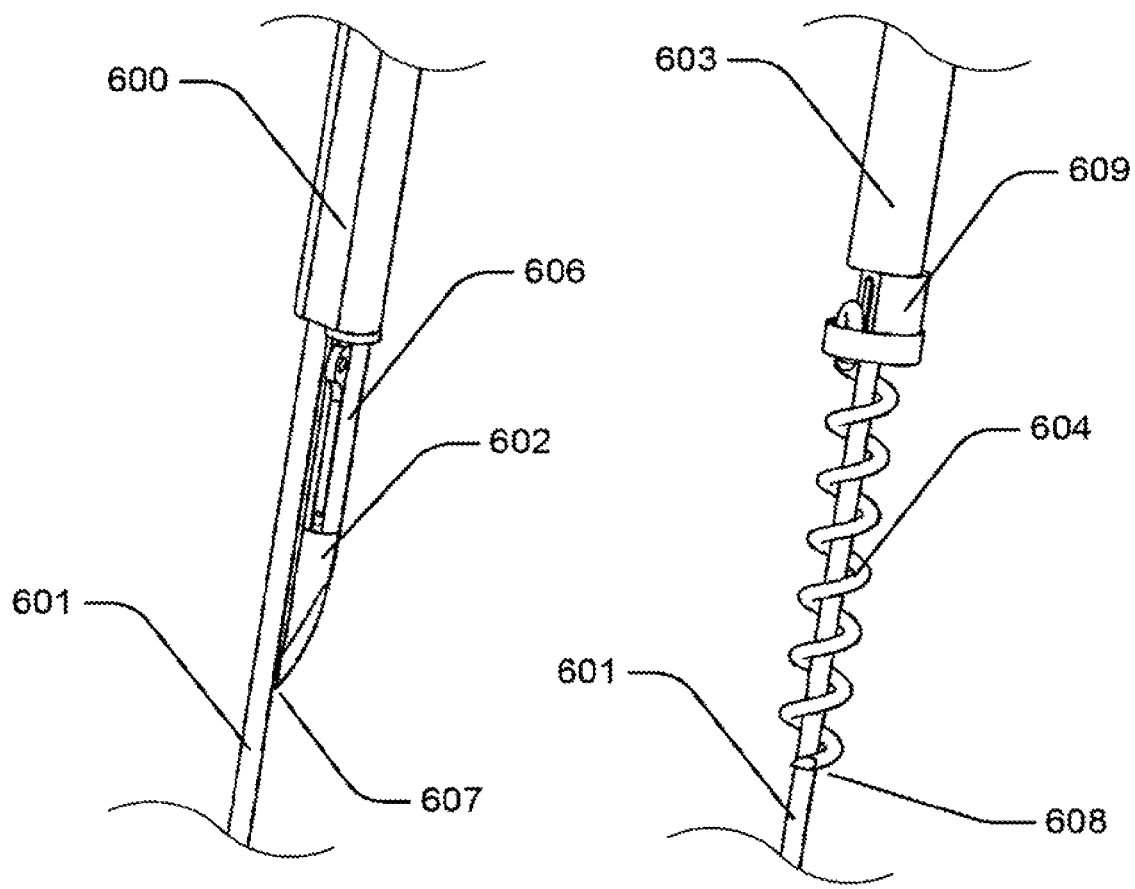
FIG. 6 is a diagram showing examples of anchors on a guided rail.

FIG. 6 shows examples of anchors guided by a rail.

Multi-lumen push tube 600 may slide over guide rail 601. Tissue anchor 602 may be temporarily attached to multi-lumen push tube 600 by constricting tube 606 and a release rod (not shown). Sliding push tube 600 along guide rail 601 enables tissue anchor 602 to be controllably delivered to a location proximate to guide rail 601. Tissue anchor 602 may be constructed or oriented in such a way that tissue anchor tip 607 slides along or very near to guide rail 601. Such orientation or construction enables the tip to be protected from obstructions in the catheter or body that may dull the tip. Also, such orientation or construction protects areas of tissue proximate the guide rail from inadvertent, damaging contact with the sharp tip 607 of tissue anchor 602.

Single-lumen push tube 603 may slide over guide rail 601. Helical tissue anchor 604 also may slide over guide rail 601 and may be temporarily attached to single-lumen push tube 603 by latch mechanism 609. Latch mechanism 609 may be fastened to anchor 604 by a friction fitting that is released under sufficient axial force. This assembly enables tissue anchor 604 to be controllably delivered to a location proximate to guide rail 601. Tissue anchor 604 may be constructed or oriented in such a way that tissue anchor tip 608 slides along or very near to guide rail 601. Such orientation or construction enables the tip to be protected from obstructions in the catheter or body that may dull the tip. Also, such orientation or construction protects areas of tissue proximate the guide rail from inadvertent, damaging contact with the sharp tip of tissue anchor 608.

FIG. 6 shows examples of two particular types of anchors being guided by a rail. However, to those skilled in the art, it is apparent that many other types of anchors could also be deployed with the aid of a guide rail as well.

Figure 7:
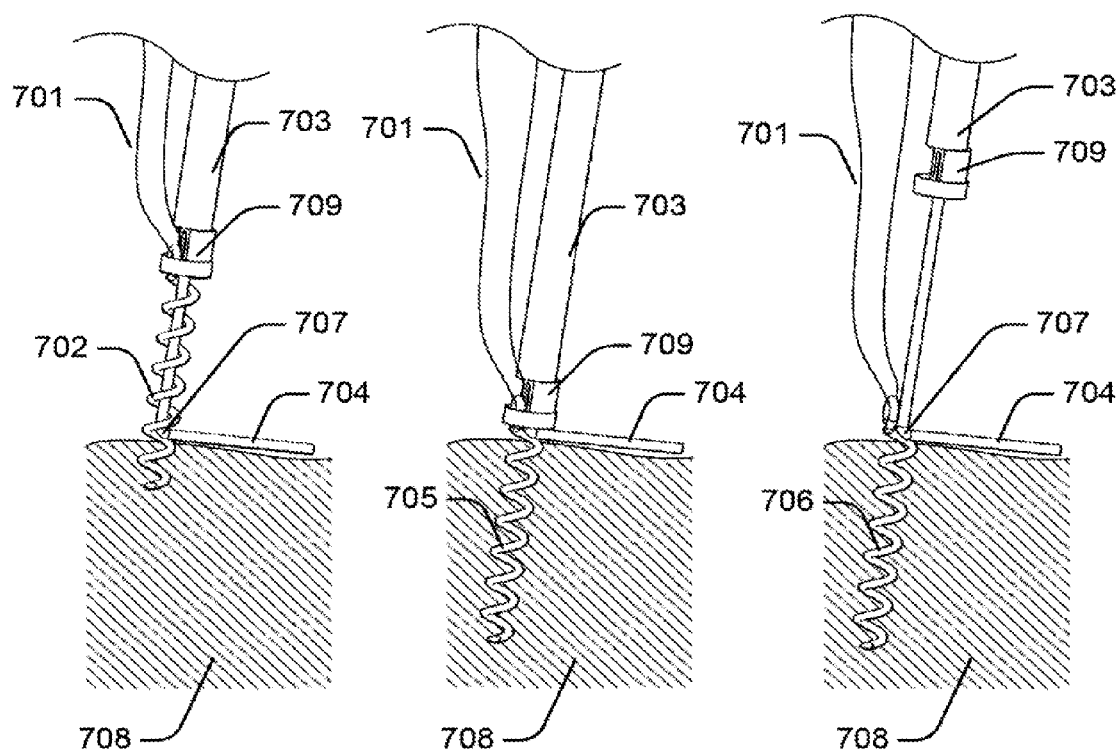
FIG. 7 is a diagram showing an example of a helical anchor on a guided rail penetrating tissue.

FIG. 7 shows a helical anchor according to one illustrated embodiment.

Helical tissue anchor 702 is shown partially deployed into tissue 708. The location that anchor 702 enters the tissue may be determined by the position of guide rail 704. Bend 707 in guide rail 704 may be positioned at the approximate location where the anchor 702 is to be deployed into the tissue. Bend 707 in guide rail 704 may comprise a hinge, a flexure, or one of many other joints. Tissue anchor 702 is deployed by rotating push tube 703. The rotation of tissue anchor 702 at the position of the bend 707 causes anchor 702 to spiral off guide rail 704 and into tissue 708.

Helical tissue anchor 705 is shown fully deployed into tissue 708, but still connected to latch mechanism 709. In the fully deployed position, anchor 705 may no longer wrap around guide rail 704. When anchor 705 is still connected to latch mechanism 709, it may be readily retracted by counter-rotating push tube 703.

Helical tissue anchor 706 is shown fully deployed into tissue 708 and disconnected from to latch mechanism 709. Latch mechanism 709 may become disconnected from anchor 706 by retracting push tube 703 or releasing latch mechanism 709 with the addition of another cable to trigger a release mechanism.

Figure 8:
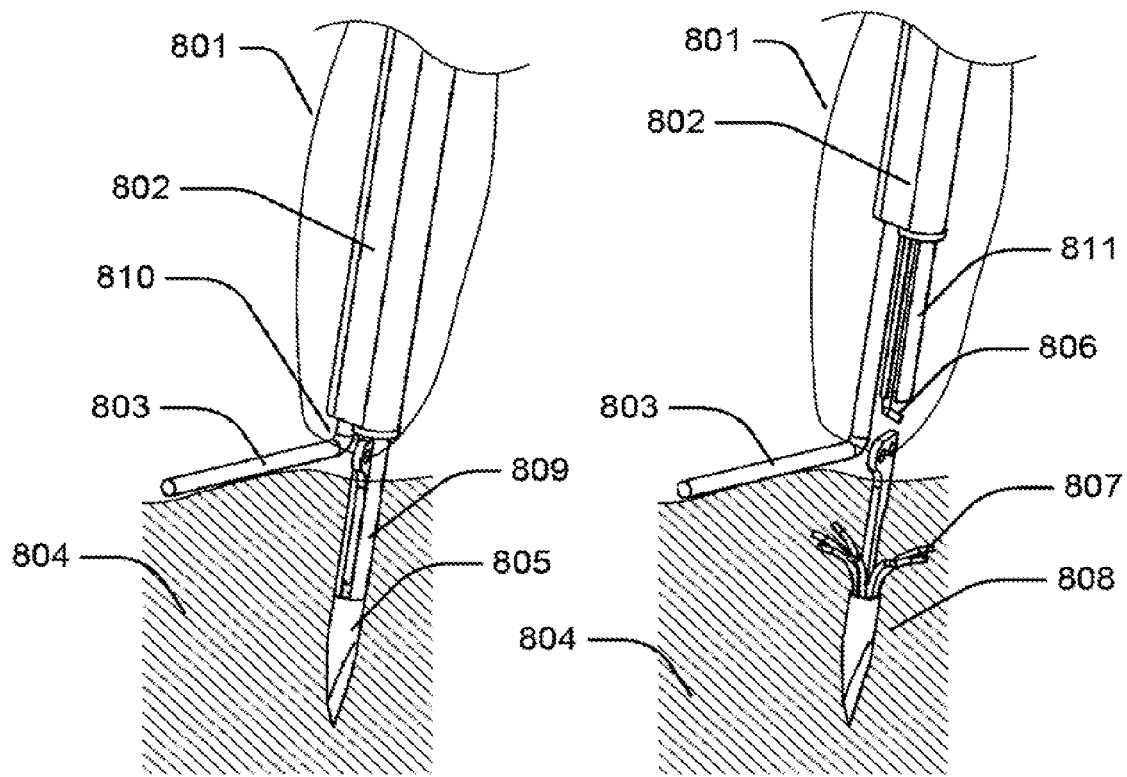
FIG. 8 is a diagram showing an example of a multi-barbed anchor on a guided rail penetrating tissue.

FIG. 8 shows an example of a multi-barbed anchor being deployed in tissue according to one illustrated embodiment.

Multi-barbed tissue anchor 805 is shown fully inserted into tissue 804, but still encapsulated by constricting tube 809. The location that anchor 805 enters the tissue may be determined by the position of guide rail 803. A bend 810 in guide rail 803 may be positioned at the approximate location where the anchor 805 is to be deployed into the tissue 804. The bend 810 in guide rail 803 may be constructed using a hinge, a flexure, or one of many other methods. Tissue anchor 805 is deployed by advancing push tube 802 over guide rail 803. If anchor 805 is encapsulated by constricting tube 809, it may be readily retracted by retracting push tube 802.

Multi-barbed tissue anchor 808 is shown fully inserted into tissue 804, but disconnected from constricting tube 811 and release rod 806. Anchor 808 is preferably retracted slightly before release rod 806 is disconnected in order to cause barbs 807 to expand. Tissue anchor 808 may be disconnected from release rod 806 and barbs 807 may be expanded by retracting constricting tube 809 relative to the release rod 806 and tissue anchor 808. Retracting constricting tube 811 past the tips of barbs 807 causes said barbs to be released and expand.

Figure 9:
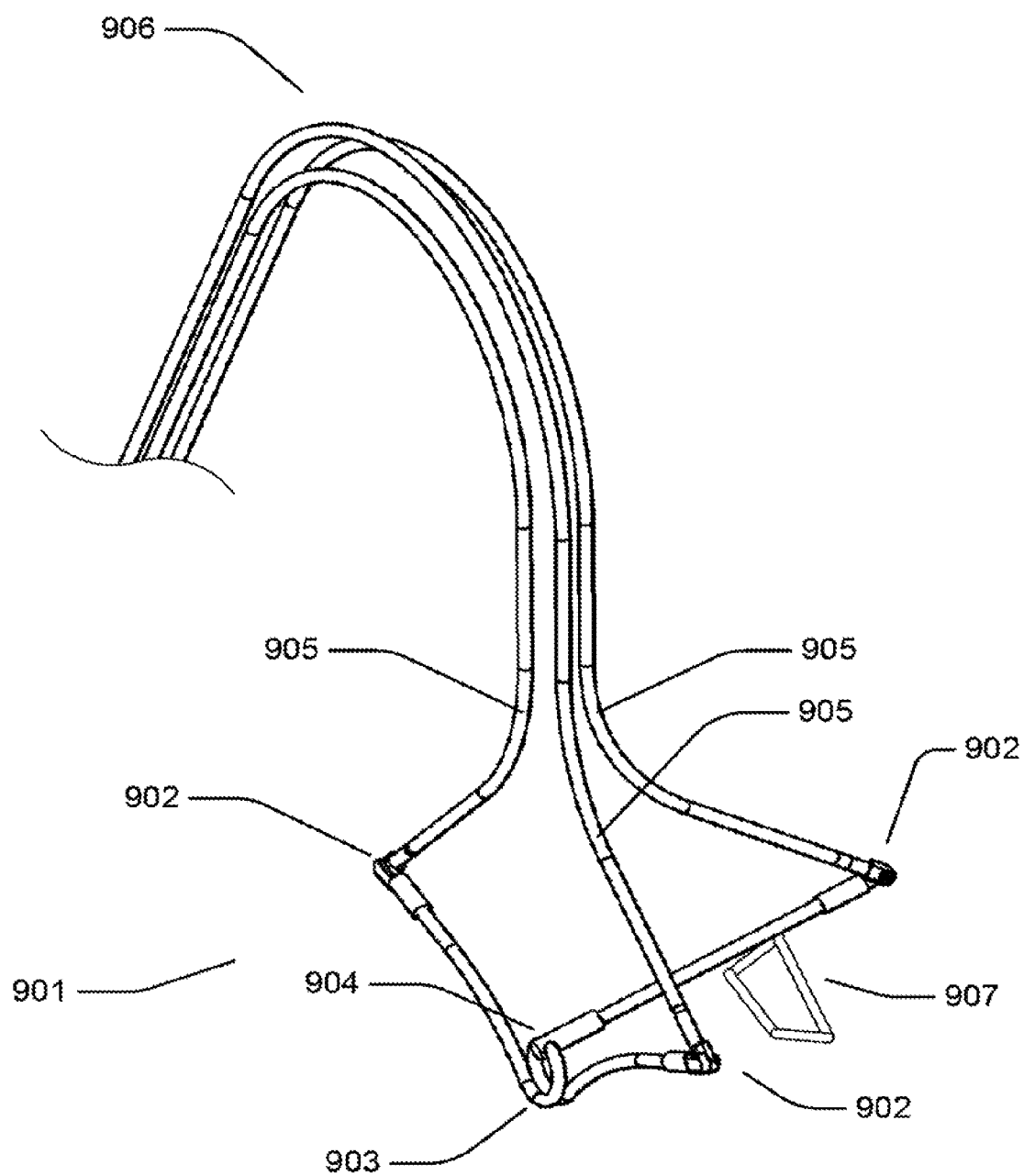
FIG. 9 is a diagram of an anchor guiding frame according to one illustrated embodiment.

FIG. 9 shows an example of an anchor guiding frame according to one illustrated embodiment.

Anchor guiding frame 901 is used to guide tissue anchors to correct insertion points. The anchor guiding frame 901 shown comprises three guide rails 905, but said frame may comprise more or fewer guide rails. The anchor guiding frame 901 embodiment given shows all guide wires 905 connected at the bottom of the frame. An anchor guiding frame is not required to have all guide wires connected together, although it is often preferable to do so to create a framework that enables anchors to be positioned relative to each other and to anatomical features. An anchor guiding frame may have multiple disconnected groups of connected guide wires.

The anchor guiding frame preferably is capable of folding to enable delivery via a catheter. Guide wires 905 may be hinged at bends 902 and guide wire connection point 904 to enable folding. Loop 903 facilitates folding and also acts as a spring to enable unfolding of the anchor guiding frame 901.

Guide wires 905 may be formed to have bend 906 when no external forces are being applied. When guide wires 905 are carried in a catheter with an articulating mechanism shaped into a curve as shown in FIG. 2, the forces exerted on the guide wire by the catheter and articulating mechanism will cause bend 906 to align with the curve in the articulating mechanism. Such alignment causes anchor guiding frame 901 to rotate to a desired position relative to the catheter orientation. Bend 906 may also be formed to assist in curving the articulating mechanism in a particular way.

An anchor guiding frame may also contain additional features which use anatomical features or movement to assist in orientation of said anchor guiding mechanism. An example of such a feature is give by alignment fin 907. Alignment fin 907 is attached rigidly to flexible anchor guiding frame 901 and shaped so that it may be deflected by an anatomical feature, such as mitral valve leaflets, to a particular orientation. As the flexible anchor guiding frame 901 is advanced toward an anatomical feature, such as the mitral valve annulus, the shape or motion of an anatomical feature, such as the mitral valve leaflets, may cause alignment fin 907, and thus flexible anchor guiding frame 901, to rotate to a desired orientation.

Figure 10:
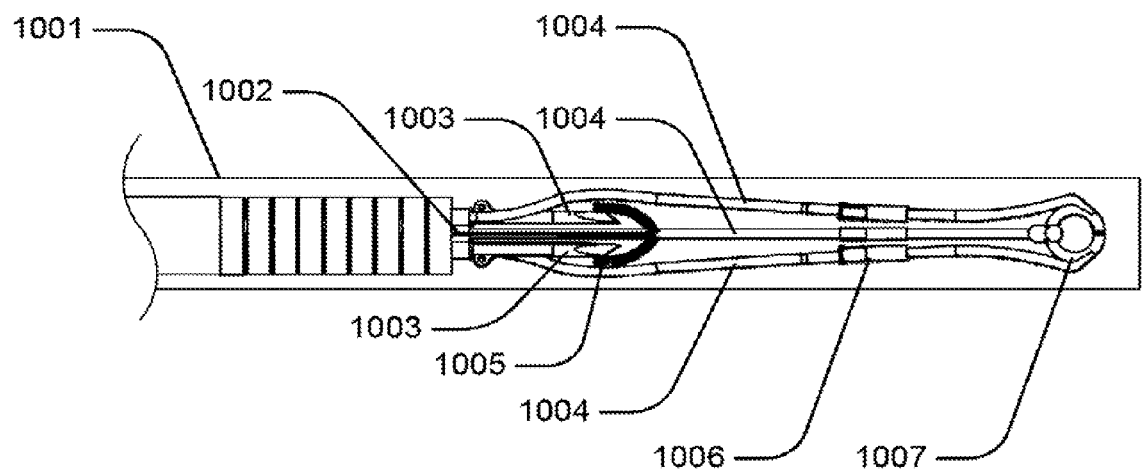
FIG. 10 is a diagram of an anchor guiding frame compressed into a sheath according to one illustrated embodiment.

FIG. 10 shows an anchor guiding frame folded for delivery inside a catheter according to one illustrated embodiment.

The anchor guiding frame comprising guide wires 1004 may be folded inside catheter 1001. Hinges 1006 and loop 1007 enhance folding of the anchor guiding mechanism. In the embodiment given, tissue anchors 1003 fit between the guide wires 1004 in the folded configuration. Protective anchor cap 1005 holds and covers the sharp tips of tissue anchors 1003 and may ensure that the tips do not catch or embed on the sides of catheter 1001. Protective anchor cap 1005 is held in place by control wire 1002

Figure 11:
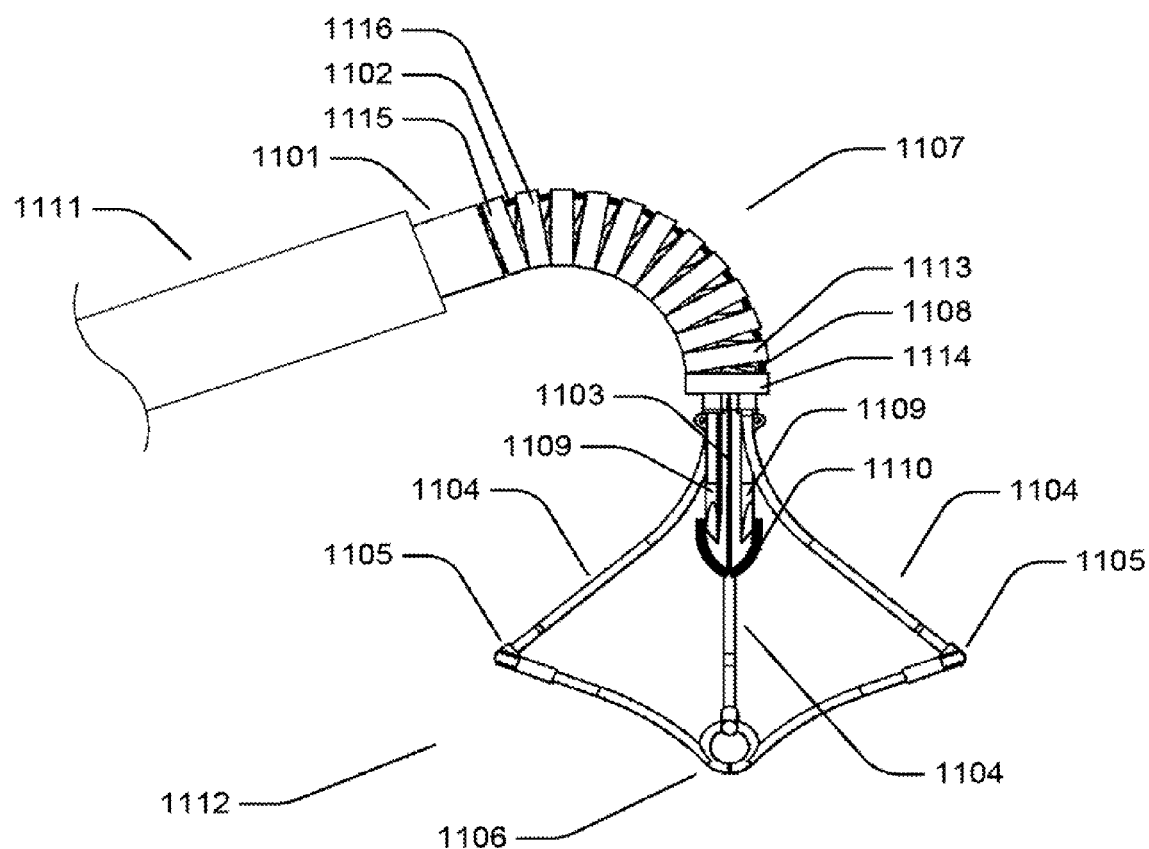
FIG. 11 is a diagram of an expanded anchor guiding frame according to one illustrated embodiment.

FIG. 11 shows an anchor guiding frame in an expanded configuration according to one illustrated embodiment.

Anchor guiding frame 1112 may self expand after exiting catheter 1111. Loop 1106 may be formed to cause said frame to expand. Hinges 1105 facilitate separation of guide wires by about 20 to 45 mm. In the given embodiment, tissue anchors 1109 are held within the volume encompassed by anchor guiding frame 1112 which ensures the anchors 1109 do not accidentally impinge tissue. Also, the tissue anchors tips are held captive within protective anchor cap 1110. The anchor tips may be released by advancing control wire 1103 and thereby also advancing anchor cap 1110. The anchor tips are no longer held captive if anchor cap 1110 is advanced sufficiently to a point past the anchor tips. As guide wires 1104 curve away from anchor cap 1110, advancing anchors 1109 causes the anchor tips to move away from and avoid anchor cap 1110.

Articulating mechanism 1107 is shown in a curved state. Articulating mechanism 1107 is curved using wires (not shown) that are carried on opposing sides relative to the longitudinal axis of said mechanism and fixed to the distal end of said mechanism. Tensioning one wire causes the articulating mechanism 1107 to arc in the direction of the side of said mechanism said tensioned wire is carried in. Using tensioned wires to curve an articulated joint as indicated is well known. However, for some situations, it is desirable to cause the gaps between links to open at a different rate. For example, when inserting articulating mechanism 1107 into the left atrium, it may be preferable to cause the distal links, such as link 1113 and link 1114, to separate or bend prior to or more than the proximal links, such as link 1115 and 1116. One embodiment to enable such an attribute is to insert springs, as indicated by 1108 and 1102, with varying spring constant k between the links. To cause the distal end of articulating mechanism 1107 to bend first, the distal links should be forced apart by springs with a higher spring constant than the springs between the proximal links. Another embodiment for enabling unequal separation of links is to control the shape of the guide wires 1104 that are routed through the articulating mechanism 1107. The guide wires should have a preformed bend with a decreasing radius of curvature in the area from proximal link 1115 to distal link 1114.

Figure 12:
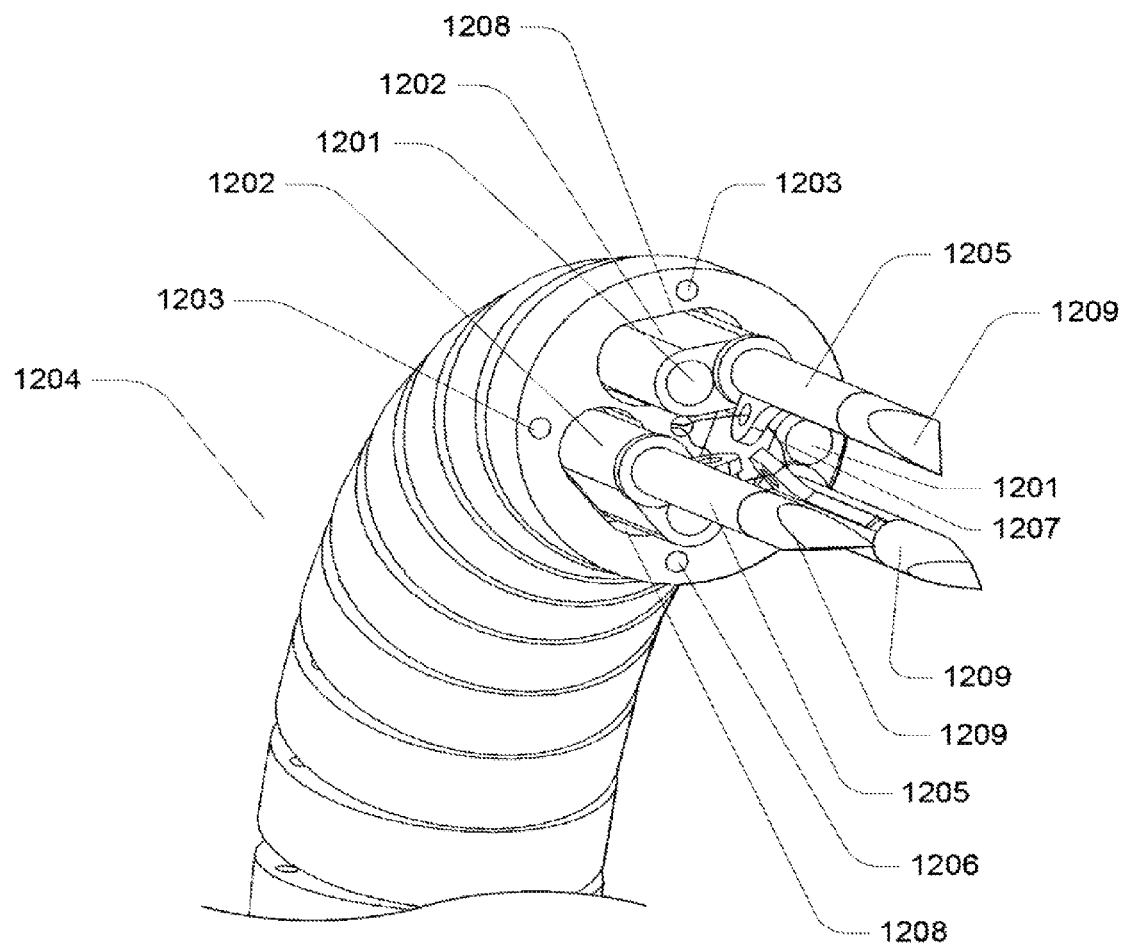
FIG. 12 is a diagram showing the distal end of the medical device according to one illustrated embodiment

FIG. 12 shows the configuration of the tissue anchors and push tubes at the distal tip of the medical apparatus according to one illustrated embodiment. For the sake of clarity, FIG. 12 omits showing guide wires and an anchor guiding frame that would typically be located at the distal tip of the medical apparatus.

The articulating mechanism 1204 may comprise multiple lumens 1208 through which push tubes 1202 are carried. In this particular embodiment, three lumens 1208 are shown, but other embodiments may comprise more or less. Push tubes 1202 may also comprise multiple lumens. In this particular embodiment, each push tube 1202 has a lumen 1201 in which a guide wire may be carried and a second lumen that carries the release rod (not shown) which is connected to the tissue anchors 1209. Constricting tubes 1205 may be mated into the distal end of said second lumen. All tissue anchors may be connected by flexible cable 1207. The flexible cable may also be carried within a separate lumen within the articulating mechanism 1204. Lumens 1203 are used to carry cables that control the curvature of the articulating mechanism 1204.

Figure 13:
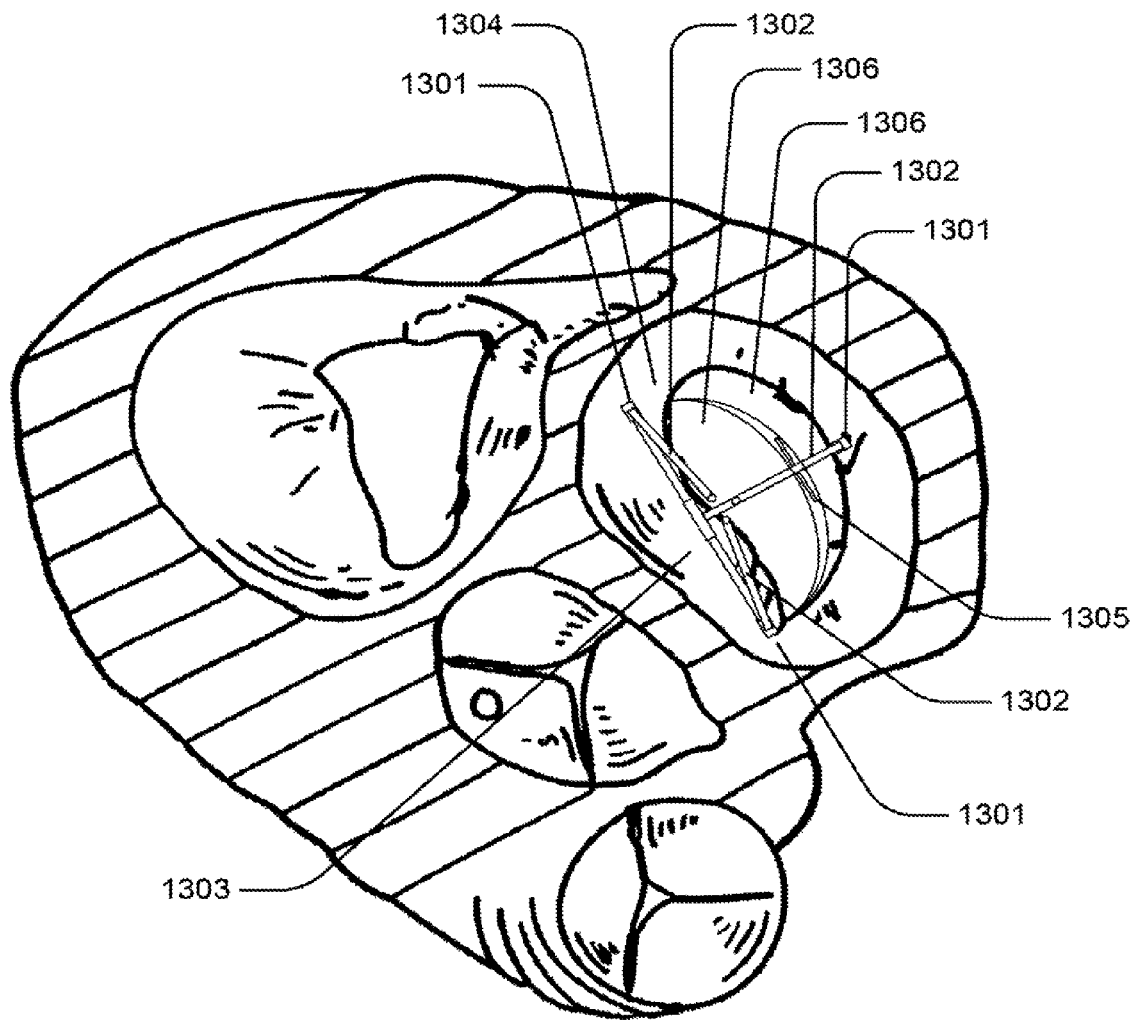
FIG. 13 is a diagram showing an example of anchors secured in a mitral valve annulus.

FIG. 13 shows a cross section of the heart with an anchor guiding frame according to one illustrated embodiment positioned within the left atrium.

Anchor guiding frame 1303 is shown self-located on the mitral annulus 1304 within the left atrium. The tissue anchor deployment sites 1301 are preferably located on the mitral annulus and coincident with bends in the guide rails 1302. FIG. 13 shows three guide rails 1302 and tissue deployment sites 1301 for simplicity; however, in many cases more deployment sites and guide rails are desirable. In such cases, it is a simple matter to add additional guide rails and anchor deployment sites to the disclosed embodiment.

Figure 14:
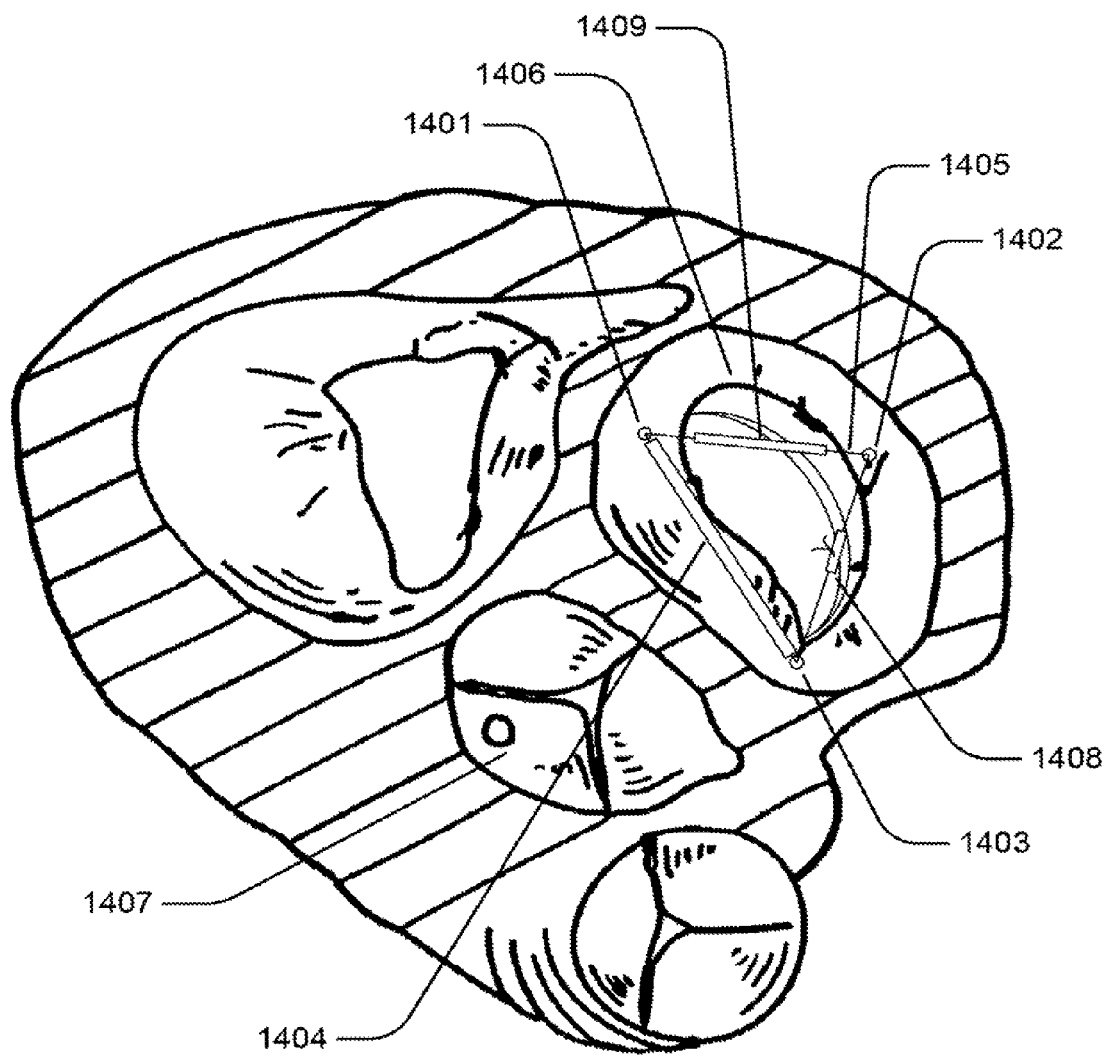
FIG. 14 is a diagram showing an example of anchors and a cable used to constrict a mitral valve annulus.

Alignment fin 1305 may fit between mitral valve leaflets 1306. The movement and anatomical structure of the mitral valve leaflets 1306 exert force on alignment fin 1305 and assist in orienting the anchor guiding frame 1303 correctly FIG. 14 shows a cross section of the heart with an installed assembly capable of constricting the mitral valve annulus according to one illustrated embodiment.

Tissue anchors 1401, 1402, and 1403 are shown fully deployed on the mitral annulus 1406. Tissue anchors may be connected by flexible cable 1405. Other mechanisms for connecting tissue anchors 1401, 1402, 1403 are possible. For example, rigid members, preferably with adjustable length, may be used to connect said anchors. Flexible cable 1405 may slide through holes on the tissue anchors 1401, 1402, 1403.

Flexible cable 1405 may pass through a hollow spreader bar 1404. Hollow spreader bar 1404 provides support to keep tissue anchors 1401 and 1403 from moving closer together when flexible cable 1405 is shortened. Such support reduces undesired forces being applied to the aortic valve 1407.

Reducing the distance between tissue anchors 1401, 1402 and 1402, 1403 causes the anterior-posterior (A-P) annular dimension of the mitral valve to reduce and improves leaflet coaptation. Several methods may be used to reduce the distance between tissue anchors. A first method is to shorten the cable during the installation procedure by routing the flexible cable 1405 through fastener 1408, pulling the cable manually to be as tight as desired and crimping fastener 1408. Fastener 1408 may also be constructed using a one way clutch so that the flexible cable 1405 can only be pulled through in one direction, in which case crimping is not required. A second method of reducing anchor separation is to include shortening actuator 1409 between two anchors. In the case where shortening actuator 1409 is included, flexible cable 1405 is split and attached to either end of the shortening actuator. One embodiment of shortening actuator 1409 contains an element that is capable of changing length as a response to changes in an external magnetic field or in response to heating induced by a changing magnetic field. The element capable of changing lengths may be made of a highly magnetostrictive alloy such as Terfenol-D or from a Shape Memory Alloy (SMA) such as specially treated Nitinol. Embodiment of such actuators are described in U.S. Ser. No. 11/902,199. The element capable of changing lengths may be made of a spring under tension encapsulated in material that melts under low heat and solidifies at body temperature—such as a thermoplastic polymer. Current induced in a loop by an external magnetic field may be channeled through the spring. The current may heat the spring which will cause the polymer to soften and the spring length to contract. The contraction of the spring can be used to reduce the separation of the tissue anchors. Embodiments of such actuators are described in U.S. Ser. No. 11/905,771.

A closed, electrically conducting loop is required if shortening actuator 1409 is to be responsive to heating or energy induced by a changing magnetic field. Such a loop may be achieved by using an electrically conductive material for flexible cable 1405 and ensuring an electrical contact between both ends of flexible cable 1405 that are connected to shortening actuator 1409.

Figure 15:
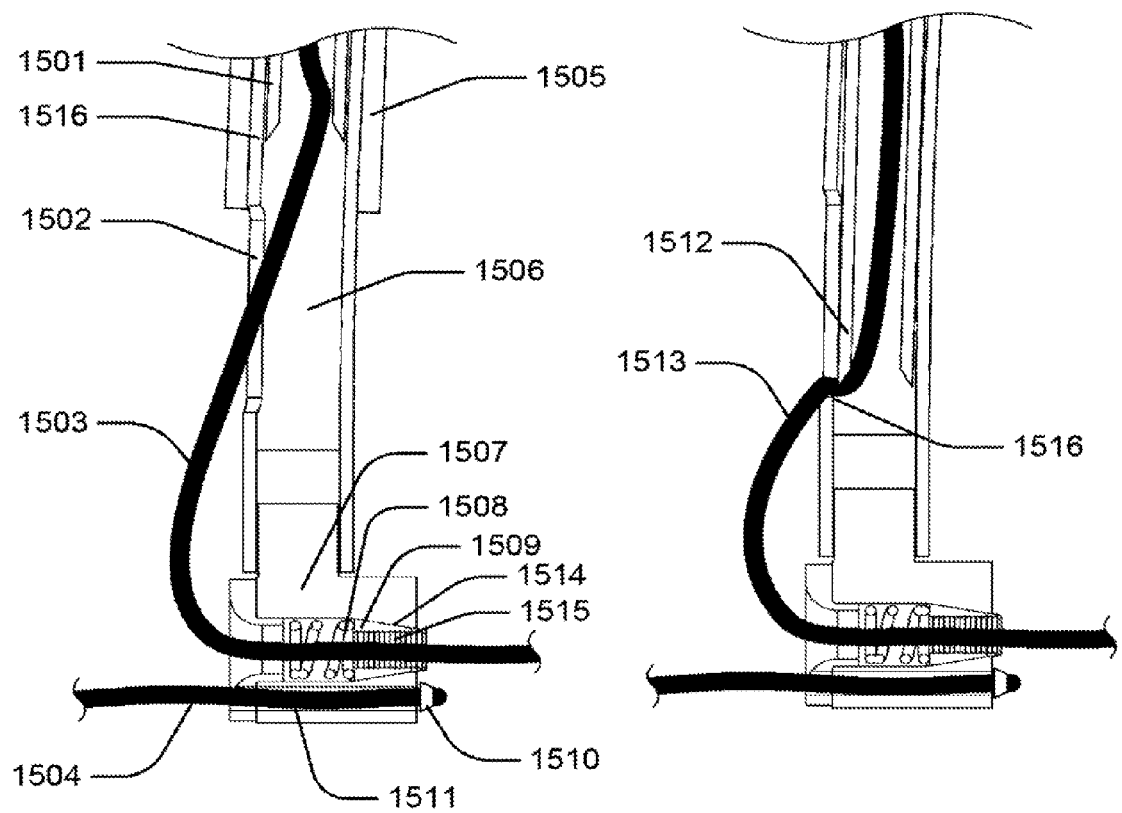
FIG. 15 is a diagram of a device for securing a cable that constricts a bodily orifice according to one illustrated embodiment.

FIG. 15 shows a cross section of a tool and fastener used to tighten and secure a cable according to one illustrated embodiment.

Fastener 1507 may be used to tighten or secure cables being used to constrict a bodily orifice. Typically prior to attachment of fastener 1507, tissue anchors have been placed, and a flexible cable has been connected to the tissue anchors. Cable end 1504 and cable end 1503 are typically carried in catheter sheath 1505 and routed outside the body. Cable end 1504 and cable end 1503 may be the two ends of one flexible cable. The portion of the cable not shown loops around the orifice to be constricted and is attached to the implanted tissue anchors used to secure the cable to the orifice.

Cable end 1504 may be fed into hole 1511 and locked by ferrule 1510 while fastener 1507 is still outside the body. Cable end 1503 may be routed through taper lock 1509 while fastener 1507 is still outside the body.

Fastener 1507 may be attached to fastener positioning tube 1506. Cable end 1503 may be inserted through slot 1502 and into fastener positioning tube 1506. Fastener 1507 and fastener positioning tube 1506 may be inserted into catheter sheath 1505 and advanced until fastener 1507 is proximate the annulus of the orifice to be constricted. Cable end 1503 may be pulled in a direction away from fastener 1507, causing the cable to pull through taper lock 1509 and constrict the orifice. While the cable is being tightened and secured, fastener 1507 may be held by fastener positioning tube 1506. Taper lock 1509 restricts cable end 1503 from being pulled out the right side of fastener 1507. Taper lock 1509 may have teeth 1515 to grip cable end 1503. Taper lock 1509 may have a longitudinal slot to enable compression of taper lock 1509 and constriction around cable end 1503. Spring 1508 may force taper lock 1509 into a conical hole 1514, causing it to tighten around cable end 1503.

When the orifice has been sufficiently constricted, cable end 1503 may be severed using cable cutting tube 1501. Cable cutting tube 1501 comprises a sharpened end 1516. Cable cutting tube 1501 is shown in a retracted position. The cable cutting tube may slide inside of fastener positioning tube 1506. Cable cutting tube 1512 is shown in the cable cutting position. Cable cutting tube 1512 may sever cable end 1513 by forcing cable end 1513 against the end of slot 1516. The cable end may be severed in other ways, including using a hot tip to melt through the cable.

Figure 16:
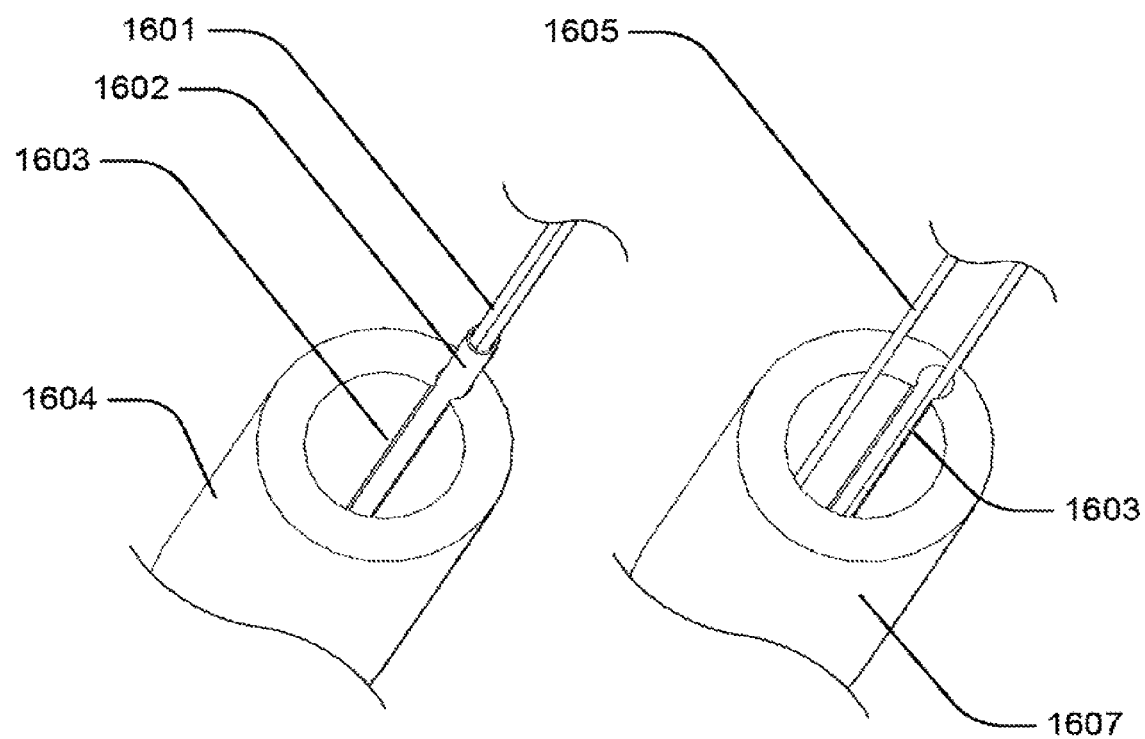
FIG. 16 is a diagram of a catheter with side slots according to one illustrated embodiment

FIG. 16 shows a catheter with grooves, or side slots, and a mechanism for securing cables or wires in said side slots according to one illustrated embodiment.

Catheter 1604 is shown with cables 1601 held within longitudinal groove 1603 on the inner surface of the tube wall by tube 1602. The longitudinal groove 1603 has a cross sectional shape that enables tube 1602 to be held captive. FIG. 16 shows a circular groove, but other shapes may be used. Tube 1602 carries cables 1601. Tube 1602 could also carry wires or tubes. When tube 1602 is removed by pulling it out the end, as shown by catheter 1607, cables 1605 are free to move into the central area of the tube. Tube 1602 can be reinserted over cables 1605 to again constrain them in groove 1603.

Although FIG. 16 shows catheter 1604 and catheter 1607 with only one groove 1603, it is possible to have many such grooves in a catheter and to secure a plurality of wires and tubes in said grooves. One of the reasons for securing cables or wires in grooves, or side slots, is to eliminate tangling of cables or wires during medical procedures.

Figure 17:
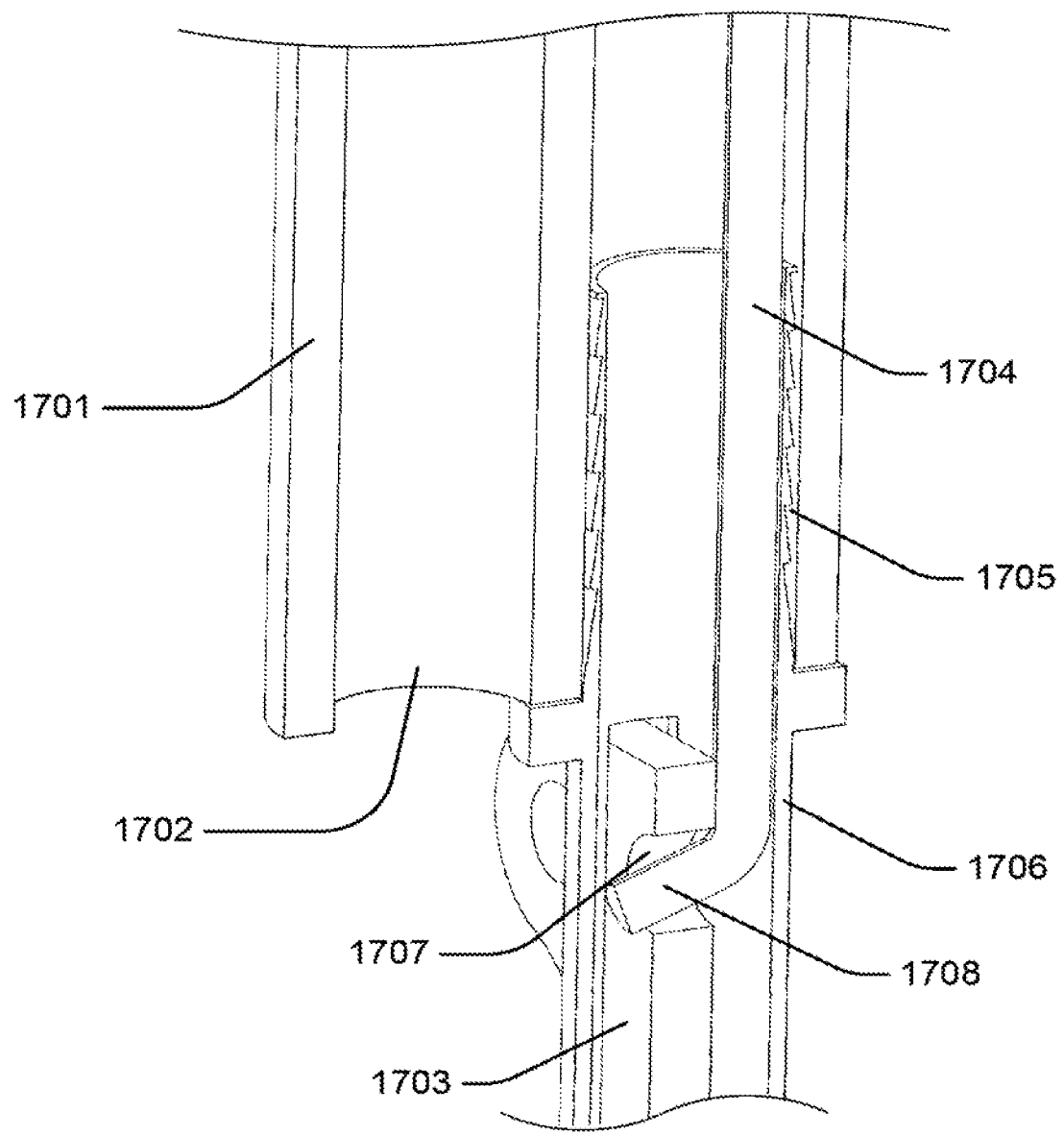
FIG. 17 is a diagram of a mechanism according to one illustrated embodiment for holding a tissue anchor captive

FIG. 17 is a cross sectional diagram of a mechanism for holding a tissue anchor captive according to one illustrated embodiment Tissue anchor 1703 may be held captive in constricting tube 1706 by release rod 1704. Constricting tube 1706 may be inserted and secured to the distal end of one lumen of push tube 1701. Constricting tube 1706 may be held captive in the lumen by ribs 1705.

Tissue anchor 1703 may be released from constricting tube 1706 by retracting push tube 1701 and constricting tube 1706 relative to release rod 1704. As the distal end of constricting tube 1706 clears hole 1707, release rod tip 1708 will pop out of hole 1707 and tissue anchor 1703 will no longer be held captive.

Lumen 1702 of push rube 1701 may be used to slide over a guide wire.

Figure 18:
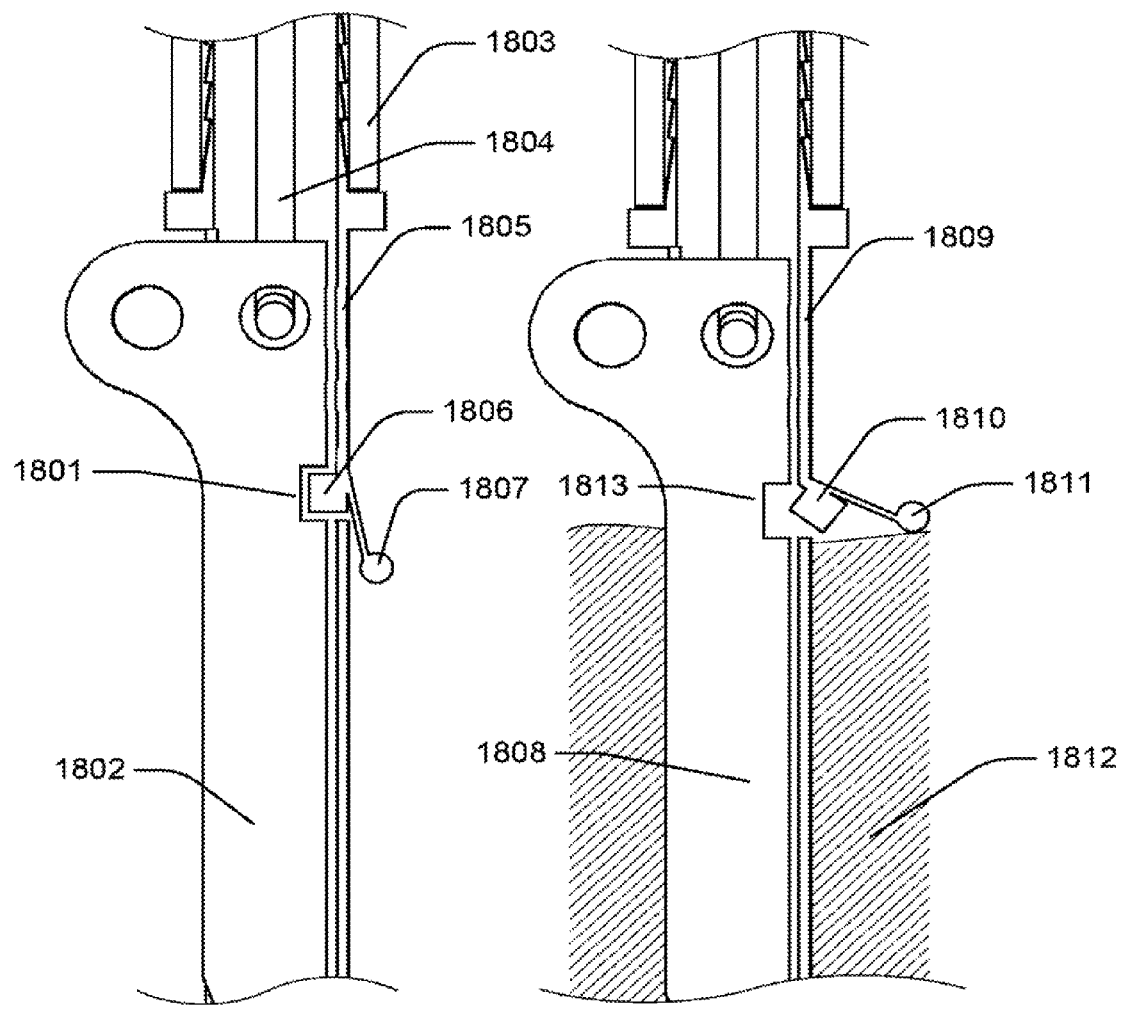
FIG. 18 is a diagram of a mechanism according to one illustrated embodiment for restricting a tissue anchor from release until said anchor is fully embedded in tissue

FIG. 18 is a cross sectional diagram of a mechanism for restricting a tissue anchor from release until anchor is fully embedded in tissue according to one illustrated embodiment An additional benefit is provided if the medical device for constricting a bodily orifice does not release tissue anchors until they are fully embedded in the tissue. It is possible to achieve this benefit by adding an additional latch 1806, 1810 to the medical device.

Tissue anchor 1802 is shown prior to deployment. Tissue anchor 1802 may not be released from constricting tube 1805 by retracting push tube 1803 and constricting tube 1805 relative to release rod 1804 because latch 1806 protrudes into notch 1801.

Tissue anchor 1808 is shown fully deployed into tissue 1812. As tissue anchor 1808 was deployed into tissue 1812, the surface of tissue 1812 causes lever 1811 to bend. When lever 1811 is bent, latch 1810 clears notch 1813. Once latch 1810 clears notch 1813, tissue anchor 1808 may be released from constricting tube 1809

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A medical system to perform percutaneous medical procedures, the medical system comprising:
   a plurality of multi-lumen push tubes, each of the multi-lumen push tubes concurrently including at least a respective first longitudinal lumen and a respective second longitudinal lumen, the respective first longitudinal lumen located entirely outside of the respective second longitudinal lumen, and the respective second longitudinal lumen located entirely outside of the respective first longitudinal lumen;
   a plurality of release rods, at least a portion of a respective one of each of the release rods movably received by the respective first longitudinal lumen of a respective one of the multi-lumen push tubes for longitudinal translation with respect thereto, the release rods selectively releasably coupled to respective ones of a plurality of tissue anchors; and
   a plurality of guide rails, at least a portion of at least a respective one of each of the guide rails moveably received by the respective second longitudinal lumen of a respective one of the multi-lumen push tubes for longitudinal translation of the respective one of the multi-lumen push tubes with respect thereto, each of the multi-lumen push tubes slideable along a respective one of the guide rails to deliver a respective one of the tissue anchors to a respective anchor position at least proximate a portion of the respective guide rail.

2. The medical system of claim 1, further comprising:
   at least one articulated mechanism including a plurality of lumens, at least a respective one of each of the multi-lumen push tubes at least partially received by a respective one of the lumens of the articulated mechanism for translation and articulation therewith.

3. The medical system of claim 1, further comprising:
   a plurality of constricting tubes, at least a respective one of each of the constricting tubes coupled to a respective one of the multi-lumen push tubes to translate therewith, at least a portion of at least a respective one of the tissue anchors received by a respective one of the constricting tubes at a first time and selectively releasable therefrom during a second time, the second time following the first time.

4. The medical system of claim 3 wherein each respective one of the tissue anchors includes a barb, and the portion of each respective one of the tissue anchors received by the respective one of the constricting tubes includes the barb of the respective one of the tissue anchors.

5. The medical system of claim 1 wherein each of the tissue anchors is physically constrained to move along the respective one of the guide rails to the respective anchor position at least proximate an end portion of the respective guide rail.

6. The medical system of claim 1 wherein each of the tissue anchors is physically constrained to move along the respective one of the guide rails to the respective anchor position at least proximate a bend portion of the respective guide rail.

7. The medical system of claim 1 wherein at least two of the guide rails are physically coupled to one another distally from the multi-lumen push tubes to form a guide frame.

8. The medical system of claim 7 wherein the guide frame includes a self-location structure arranged to physically interact with leaflets of an anatomical valve to self locate the guide frame.

9. The medical system of claim 1, further comprising:
   at least one tensionable cable that physically couples at least two of the tissue anchors to form a constricting assembly.

10. The medical system of claim 9, further comprising:
    at least one fastener that selectively physically fastens the at least one tensionable cable under tension.

11. The medical system of claim 9, further comprising:
    at least one actuator physically coupled to the at least one tensionable cable, the at least one actuator responsive to an applied stimulus to change a dimension of the at least one actuator.

12. The medical system of claim 11 wherein the at least one actuator is responsive to a magnetic field.

13. The medical system of claim 9, further comprising:
    at least one spreader physically coupled to the at least one tensionable cable between at least a pair of the tissue anchors to fix a distance therebetween.

14. The medical system of claim 1 wherein each tissue anchor of the tissue anchors includes a hole which releasably receives a portion of a respective one of the release rods, the portion of the respective one of the release rods removed from the hole when the respective one of the release rods is physically uncoupled from the respective tissue anchor.

15. A method of operating a medical system to perform percutaneous medical procedures, the method comprising:
    percutaneously delivering at least a portion of a device to a bodily organ, the portion of the device including a plurality of multi-lumen push tubes each concurrently including at least a respective first longitudinal lumen and a respective second longitudinal lumen other than the respective first longitudinal lumen; a plurality of release rods, at least a portion of each release rod movably received by the respective first longitudinal lumen of a respective one of the multi-lumen push tubes for longitudinal translation with respect thereto, each of the release rods selectively releasably coupled to a respective one of a plurality of tissue anchors; and a plurality of guide rails, at least a portion of at least a respective one of each of the guide rails movably received by the respective second longitudinal lumen of a respective one of the multi-lumen push tubes for longitudinal translation of the respective one of the multi-lumen push tubes with respect thereto, the respective second longitudinal lumen of each of the multi-lumen push tubes slideable along a respective one of the guide rails to cause movement of at least the respective first longitudinal lumen and to deliver a respective one of the tissue anchors to a respective anchor position at least proximate a portion of the respective guide rail;

positioning each of the guide rails with respect to the respective anchor position on tissue of the bodily organ;

advancing the multi-lumen push tubes along the guide rails at least until the tissue anchors are at least partially embedded in the tissue; and causing the release rods to release the tissue anchors while the tissue anchors are at least partially embedded in the tissue.

16. The method of claim 15, further comprising:
withdrawing the multi-lumen push tubes after causing the release rods to release the tissue anchors.

17. The method of claim 15 wherein at least one tensionable cable physically couples at least two of the tissue anchors, and the method further comprises:
tensioning the at least one tensionable cable to constrict an orifice in the tissue.

18. The method of claim 17, further comprising:
securing at least one fastener to the tensioned at least one tensionable cable to physically fasten the at least one tensionable cable under tension.

19. The method of claim 17 wherein at least one actuator is physically coupled to the at least one tensionable cable, and the method further comprises:
applying a stimulus to the at least one actuator to change a dimension of the at least one actuator.

20. The method of claim 19 wherein the applying the stimulus to the at least one actuator includes applying a magnetic field externally from the bodily organ.

21. The medical system of claim 14 further comprising:
a plurality of constricting tubes, each of the constricting tubes including a slot sized to receive a portion of a respective one of the tissue anchors with the hole extending therefrom.

22. The medical system of claim 21 wherein each constricting tube of the constricting tubes constricts a number of barbs of the respective one of the tissue anchors.

23. A medical system to perform a percutaneous medical procedure, the medical system comprising:
a plurality of multi-lumen push tubes, each of the multi-lumen push tubes concurrently including at least a respective first longitudinal lumen and a respective second longitudinal lumen side-by-side with the respective first longitudinal lumen;
a plurality of release rods, each release rod of the plurality of release rods including a first end and a second end, the second end including a bent portion that includes a bend in the release rod, at least a portion of a respective one of each of the release rods movably received by the respective first longitudinal lumen of a respective one of the multi-lumen push tubes for longitudinal translation with respect thereto, each one of the release rods selectively releasably coupled to the bent portion to a respective one of a plurality of tissue penetrating anchors, to selectively completely decouple the release rod from the respective one of the plurality of tissue penetrating anchors at least when the respective one of the tissue penetrating anchors is positioned at a respective anchor position, leaving no portion of the release rods attached to the respective tissue penetrating anchor; and a plurality of guide rails, at least a portion of at least a respective one of each of the guide rails moveably received by the respective second longitudinal lumen of a respective one of the multi-lumen push tubes for longitudinal translation of the respective one of the multi-lumen push tubes with respect thereto, the respective second longitudinal lumen of each of the multi-lumen push tubes slideable along a respective one of the guide rails to move at least the respective first longitudinal lumen and to deliver a respective one of the tissue penetrating anchors to the respective anchor position at least proximate a portion of the respective guide rail.

24. A medical system to perform percutaneous medical procedures, the medical system comprising:
a plurality of multi-lumen push tubes, each of the multi-lumen push tubes concurrently including at least a respective first longitudinal lumen and a respective second longitudinal lumen other than the respective first longitudinal lumen;
a plurality of tissue anchors, each of the tissue anchors movably received by and extendable from the respective first longitudinal lumen of a respective one of the multi-lumen push tubes; and
a plurality of guide rails, at least a portion of at least a respective one of each of the guide rails moveably received by the respective second longitudinal lumen of a respective one of the multi-lumen push tubes for longitudinal translation of the respective one of the multi-lumen push tubes with respect thereto, the respective second longitudinal lumen of each of the multi-lumen push tubes slideable along a respective one of the guide rails to cause movement of at least the respective first longitudinal lumen and to deliver a respective one of the tissue anchors to a respective anchor position at least proximate a portion of the respective guide rail.

25. The method of claim 15 wherein, for each multi-lumen push tube of the plurality of multi-lumen push tubes, the respective first longitudinal lumen is located entirely outside of the respective second longitudinal lumen, and the respective second longitudinal lumen is located entirely outside of the respective first longitudinal lumen.

26. The medical system of claim 23 wherein, for each multi-lumen push tube of the plurality of multi-lumen push tubes, the respective first longitudinal lumen is located entirely outside of the respective second longitudinal lumen, and the respective second longitudinal lumen is located entirely outside of the respective first longitudinal lumen.

27. The medical system of claim 24 wherein, for each multi-lumen push tube of the plurality of multi-lumen push tubes, the respective first longitudinal lumen is located entirely outside of the respective second longitudinal lumen, and the respective second longitudinal lumen is located entirely outside of the respective first longitudinal lumen.

* * * * *